United States Patent
Nishizawa et al.

(10) Patent No.: US 9,522,014 B2
(45) Date of Patent: Dec. 20, 2016

(54) MULTI-DEGREE-OF-FREEDOM FORCEPS

(71) Applicant: OLYMPUS CORPORATION, Tokyo (JP)

(72) Inventors: Koji Nishizawa, Tokyo (JP); Kazuo Banju, Tokyo (JP); Tatsutoshi Hashimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/873,554

(22) Filed: Apr. 30, 2013

(65) Prior Publication Data

US 2013/0317522 A1    Nov. 28, 2013

Related U.S. Application Data

(63) Continuation of application No. PCT/JP2012/072986, filed on Sep. 7, 2012.
(Continued)

(51) Int. Cl.
*A61B 17/00* (2006.01)
*A61B 17/29* (2006.01)
*A61B 17/34* (2006.01)

(52) U.S. Cl.
CPC ........... *A61B 17/29* (2013.01); *A61B 17/2909* (2013.01); *A61B 17/3423* (2013.01);
(Continued)

(58) Field of Classification Search
CPC ......... A61B 17/29; A61B 19/20; A61B 19/22; A61B 2017/00424; A61B 2019/2246; A61B 2017/2927; A61B 2019/2242; A61B 5/055; A61B 17/0469; A61B 17/062; A61B 17/34; A61B 2017/2901; A61B 2017/2902; A61B 2017/2909;A61B 2017/291; A61B 2017/2919; A61B 2017/292; A61B 2017/2926; A61B 2017/2929; A61B 2017/2939; A61B 2017/2946; A61B 2017/347
(Continued)

(56) References Cited

U.S. PATENT DOCUMENTS

2007/0250113 A1   10/2007 Hegeman et al.
2008/0188871 A1*   8/2008 Smith et al. .................. 606/139
(Continued)

FOREIGN PATENT DOCUMENTS

EP          2 430 991 A1    3/2012
JP       A-2006-20806       1/2006
(Continued)

OTHER PUBLICATIONS

Dec. 11, 2012 International Search Report issued in International Patent Application No. PCT/JP2012/072986.
(Continued)

*Primary Examiner* — Katherine M Shi
*Assistant Examiner* — Lindsey Bachman
(74) *Attorney, Agent, or Firm* — Oliff PLC

(57) ABSTRACT

A multi-degree-of-freedom forceps includes a insertion portion that has a first bending portion and a second bending portion connected to each other at both ends via an operating member; a treatment portion that is attached to the first bending portion and is used for tissue treatment; and an operating portion that is attached to the second bending portion to bend the second bending portion to thereby bend the first bending portion. The operating portion has a handle body capable of being swung relative to the insertion portion with the second bending portion as an operation center. The handle body has a grip portion that is gripped by a user in use. The grip portion is provided around the operation center or closer to the insertion portion side than the operation center.

20 Claims, 35 Drawing Sheets

Related U.S. Application Data

(60) Provisional application No. 61/532,244, filed on Sep. 8, 2011.

(52) U.S. Cl.
CPC . *A61B 2017/003* (2013.01); *A61B 2017/0046* (2013.01); *A61B 2017/00424* (2013.01); *A61B 2017/291* (2013.01); *A61B 2017/292* (2013.01); *A61B 2017/293* (2013.01); *A61B 2017/2906* (2013.01); *A61B 2017/2908* (2013.01); *A61B 2017/2927* (2013.01); *A61B 2017/2929* (2013.01); *A61B 2017/347* (2013.01); *A61B 2017/3445* (2013.01); *A61B 2017/3466* (2013.01)

(58) Field of Classification Search
USPC ....... 606/205–207, 1, 124; 604/164.01, 264; 74/10, 10.8, 98, 89, 505, 490.01, 490.02, 74/490.066
See application file for complete search history.

(56) References Cited

U.S. PATENT DOCUMENTS

| | | | | |
|---|---|---|---|---|
| 2009/0005738 | A1* | 1/2009 | Franer | 604/164.01 |
| 2009/0299344 | A1* | 12/2009 | Lee | A61B 17/062 606/1 |
| 2010/0041945 | A1* | 2/2010 | Isbell, Jr. | 600/104 |
| 2010/0249497 | A1* | 9/2010 | Peine et al. | 600/104 |
| 2011/0106146 | A1* | 5/2011 | Jeong | 606/208 |
| 2012/0041450 | A1* | 2/2012 | Awtar et al. | 606/130 |

FOREIGN PATENT DOCUMENTS

| | | |
|---|---|---|
| JP | A-2008-520362 | 6/2008 |
| JP | A-2009-538186 | 11/2009 |
| JP | A-2010-500149 | 1/2010 |
| JP | A-2010-503457 | 2/2010 |
| JP | A-2010-154895 | 7/2010 |
| JP | A-2011-509112 | 3/2011 |
| JP | A-2011-152450 | 8/2011 |
| WO | WO 2006/073581 A2 | 7/2006 |
| WO | WO 2007/139734 A2 | 12/2007 |
| WO | WO 2008/020964 A2 | 2/2008 |
| WO | WO 2008/033240 A2 | 3/2008 |
| WO | WO 2009/088430 A1 | 7/2009 |
| WO | 2009/098244 A2 | 8/2009 |
| WO | 2010/096580 A1 | 8/2010 |
| WO | 2011/070846 A1 | 6/2011 |

OTHER PUBLICATIONS

Jan. 13, 2015 Search Report issued in European Application No. 12829948.4.

* cited by examiner

MULTI-DEGREE-OF-FREEDOM FORCEPS

This application is a continuation based on U.S. Patent Application No. 61/532,244 provisionally applied in the United States on Sep. 8, 2011 and PCT/JP2012/072986, filed on Sep. 7, 2012. The contents of both the United States Patent Application and the PCT Application are incorporated herein by reference.

TECHNICAL FIELD

The present invention relates to a multi-degree-of-freedom forceps capable of bending a distal end side of an insertion portion provided with a treatment portion.

BACKGROUND ART

In the related art, in laparoscopic surgery or the like, forceps are used in order to perform various procedures within a body cavity. As one of such forceps, there is known a multi-degree-of-freedom (hereinafter, refer to DOF) forceps that enables bending of a distal end side of a long insertion portion inserted into a body cavity in order to increase the degree of freedom of operations of a treatment portion used to perform a procedure, within a body cavity.

For example, PCT International Publication No. WO2009/088430 discloses a multi-DOF forceps including bending portions at both ends of a long and rigid insertion portion. The two bending portions have a well-known structure in which bending pieces or joint rings are arranged side by side in an axis direction and are connected to each other by an operating member, such as a wire. A treatment portion is connected to one of end portions of the insertion portion and an operating portion is connected to the other. If a user operates a handle or the like of the operating portion to bend the bending portion (second bending portion) closer to the operating portion in a desired direction, the operating member connected to the second bending portion advances and retreats in the axis direction. As a result, the bending portion (first bending portion) distant from the operating portion can be bent in a direction opposite to the second bending portion so as to direct the treatment portion to an intended direction.

When the multi-DOF forceps is used, the insertion portion is inserted into a body cavity from an access port, such as a trocar attached to a patient so as to pass through a body wall, a tissue, or the like. The user moves the treatment portion at the distal end of the insertion portion to a desired position to perform a procedure, using generally three operations including the above-described bending operation, the advance/retreat operation of the insertion portion relative to the access port, and an swinging operation (pivot operation) of the insertion portion having the access port as an operation center.

SUMMARY OF THE INVENTION

A first aspect of the present invention includes a insertion portion which is longitudinal, extends along a longitudinal axis and has a joint portion at a proximal end portion; an operating portion which has a handle body that is coupled to the joint portion so as to be rotatable in a direction intersecting the longitudinal axis of the insertion portion and that is provided so as to be capable of swinging and operating relative to the insertion portion; a bending portion which is provided at a distal end portion of the insertion portion so as to be bendable according to the swinging operation of the handle body relative to the insertion portion; a bending locking mechanism which enables fixation of the rotation of the insertion portion in the direction intersecting the longitudinal axis of the insertion portion relative to the handle body, and release of the fixation; an access port which has a pivot portion that supports the insertion portion so as to be movable along the longitudinal axis and supports the insertion portion so as to be pivotally operable and that is mountable on a body wall; a pivot locking mechanism which enables fixation of the pivot operation of the insertion portion relative to the pivot portion and the movement of the insertion portion in the direction along the longitudinal axis, and release of the fixation; and a switching operating portion which performs switching between a state where the fixation by the bending locking mechanism is released and the fixation by the pivot locking mechanism is performed, and a state where the fixation by the bending locking mechanism is performed and the fixation by the pivot locking mechanism is released.

According to a second aspect of the present invention, in the first aspect, the switching operating portion may further perform switching to a state where the fixation by the bending locking mechanism is released and the fixation by the pivot locking mechanism is released.

According to a third aspect of the present invention, in the first aspect, a distal end portion of a locking member of the bending locking mechanism may be provided so as to be movable from a position apart from the joint portion to a position where the distal end portion of the locking member is locked to the joint portion, and as the distal end portion of the locking member is locked to the joint portion, the locking member may fix the handle body to the insertion portion in the direction intersecting the longitudinal axis of the insertion portion.

According to a fourth aspect of the present invention, in the first aspect, a movable member of the pivot locking mechanism may be provided so as to be movable from a position apart from the pivot portion to a position where the pivot portion is pressed, and as the movable member presses the pivot portion, the fixation by the pivot locking mechanism may be performed.

According to a fifth aspect of the present invention, in the first aspect, the multi-degree-of-freedom forceps may further include a treatment portion that is attached to the bending portion and is used for tissue treatment, the operating portion may have a rotating knob that is provided apart from the longitudinal axis of the insertion portion and rotates the treatment portion relative to the insertion portion, and the rotating knob may be connected to the treatment portion via a shaft having flexibility.

According to a sixth aspect of the present invention, in the first aspect, the operating portion may be attached to the joint portion so as to be capable of swinging relative to the insertion portion with the second bending portion as an operation center, the joint portion may have a spherical first member, and a spherical second member that is attached so as to be rotatable around a first rotation axis of the first member, and the handle body may be attached so as to be rotatable around a second rotation axis of the second member orthogonal to the first rotation axis.

According to a seventh aspect of the present invention, in the sixth aspect, an outer periphery of the first member may be formed with a first engaging protrusion, an outer periphery of the second member may be formed with a second engaging protrusion, the first member and the second member may be arranged so that a first plane including the first engaging protrusion and a second plane including the second engaging protrusion intersect each other, and the bending direction of the bending portion may be regulated so that the bending portion bends along the first plane and the second plane.

According to a eighth aspect of the present invention, in the first aspect, the operating portion may be attached to the insertion portion via a biaxial gimbal structure.

According to a ninth aspect of the present invention, in the first aspect, the switching state of the switching operating portion is maintained even if a user removes user's hand from the switching operating portion.

According to a tenth aspect of the present invention, in the first aspect, the pivot portion includes a first tubular portion and a second tubular portion that are fittable to each other and a spherical portion that has a through hole and is arranged in a lumen of the first tubular portion and the second tubular portion so as to be held by the first tubular portion and the second tubular portion.

According to an eleventh aspect of the present invention, in the first aspect, a radial cross-section of the insertion portion is a non-circular and is impossible to rotate relative to the access port attached to a patient.

According to a twelfth aspect of the present invention, in the tenth aspect, a radial cross-section of the insertion portion is a non-circular and is impossible to rotate relative to the spherical portion, and if a force equal to or more than a predetermined value is applied, the insertion portion rotates relative to the first tubular portion and the second tubular portion together with the spherical portion.

According to a thirteenth aspect of the present invention, in the tenth aspect, the insertion portion may be inserted through the access port attached to a patient and introduced into a body cavity of the patient, the pivot locking mechanism may be configured to include the spherical portion, and a rail member attached to the insertion portion, and the spherical portion may have a bearing that reduces the advance or retreat resistance of the insertion portion inserted through the through hole.

According to a fourteenth aspect of the present invention, in the tenth aspect, the pivot portion may have an airtight portion that is provided in the lumen of at least one of the first tubular portion and the second tubular portion and maintains an airtight state of an inner cavity of the access port.

According to a fifteenth aspect of the present invention, in the tenth aspect, the pivot portion may be detachable relative to the access port.

According to a sixteenth aspect of the present invention, in the tenth aspect, the access port may have an airtight portion that maintains an airtight state of a lumen of the access port when the pivot portion is not attached.

According to a seventeenth aspect of the present invention, in the first aspect, the multi-degree-of-freedom forceps may further include a treatment portion which is attached to the bending portion and is used for tissue treatment, the treatment portion may have a pair of forceps pieces that are opened and closed, the operating portion may have a second operating portion that is connected to the pair of forceps pieces and opens and closes the forceps pieces, and the second operating portion may be rotatably attached to the handle body.

According to a eighteenth aspect of the present invention, in the first aspect, the multi-degree-of-freedom forceps may further include a treatment portion which is attached to the bending portion and is used for tissue treatment, the operating portion may have a rotating knob that rotates the treatment portion relative to the insertion portion, and the rotating knob may be connected to the treatment portion at a position closer to a distal end side than a proximal end portion of the insertion portion.

According to a nineteenth aspect of the present invention, in the first aspect, the operating portion may have a grip portion that is provided around the joint portion and is elastically deformable, and the frictional force between the grip portion and the joint portion may change when the grip portion is elastically deformed to change contact pressure with the joint portion.

PREFERRED EMBODIMENTS

Hereinafter, a first embodiment of the present invention will be described with reference to FIGS. 1 to 30.

Basic Structure

Figure 1:
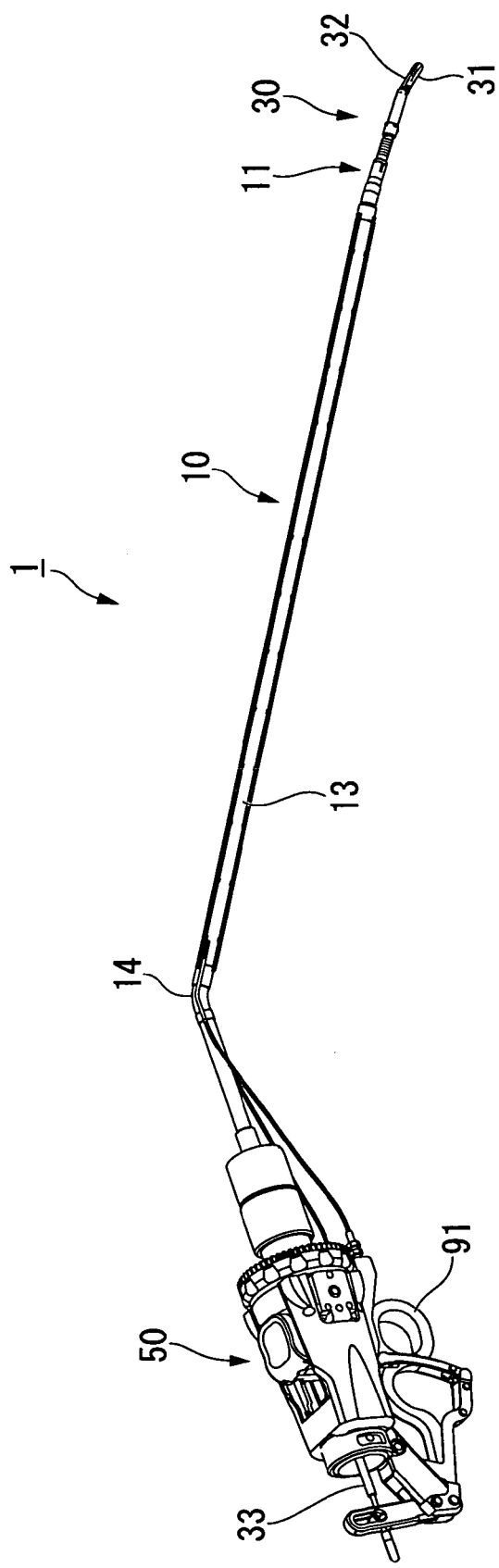
FIG. 1 is an overall view of a multi-degree-of-freedom forceps of a first embodiment of the present invention.

FIG. 1 is a view showing the overall configuration of a multi-DOF forceps 1 of the present embodiment. The multi-DOF forceps 1 includes a long rigid insertion portion 10, an operating portion 50 provided on the proximal end side of the insertion portion 10, a first bending portion (bending portion) 11, a bending locking mechanism 150, an access port 100, a pivot locking mechanism 160, and a locking lever (switching operating portion) 81. The detailed configuration of them will be described below.

Additionally, the multi-DOF forceps 1 may include a treatment portion 30 that is attached to the first bending portion 11 and is used for tissue treatment.

Figure 5A:
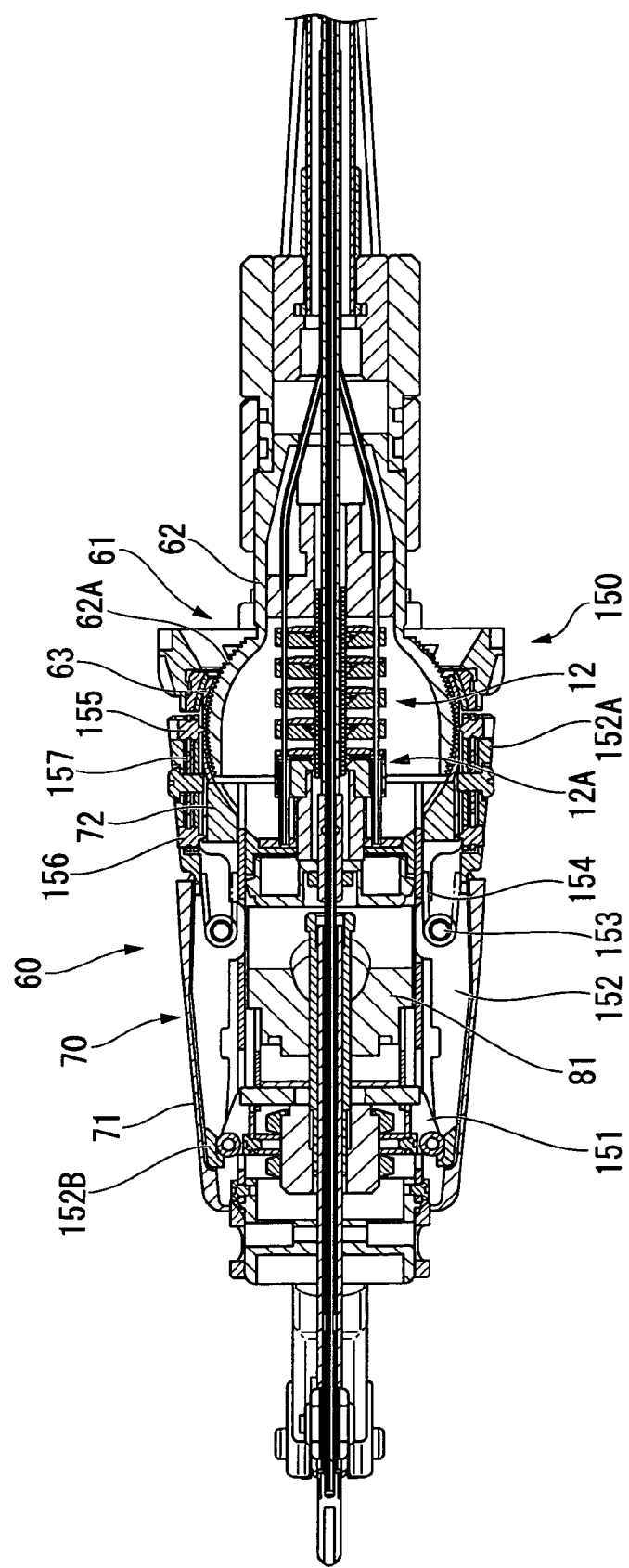
FIG. 5A is a cross-sectional view of a first operating portion of the multi-degree-of-freedom forceps.

The basic structure regarding the bending operation of the insertion portion 10 is the same as that described in the above PCT International Publication No. WO2009/088430, and includes the first bending portion 11 on the distal end side and a second bending portion 12 on the proximal end side, which are connected to each other by four operating members (refer to FIG. 5A). The insertion portion 10 includes an outermost outer pipe 13 and a plurality of pipes that are inserted through and coaxially arranged in the outer pipe 13. One of the plurality of pipes is a rotation operating pipe (to be described below) connected to the treatment portion 30, and extends to the inside of the operating portion 50 through the inside of the outer pipe 13. Additionally, the insertion portion 10 is bent at a curved portion 14 that is curved so as to be easily operated even if a plurality of multi-DOF forceps are inserted through one access port (to be described below). The curved angle and number of curved portions can be appropriately set in consideration of the operation aspects of the multi-DOF forceps.

Figure 2:
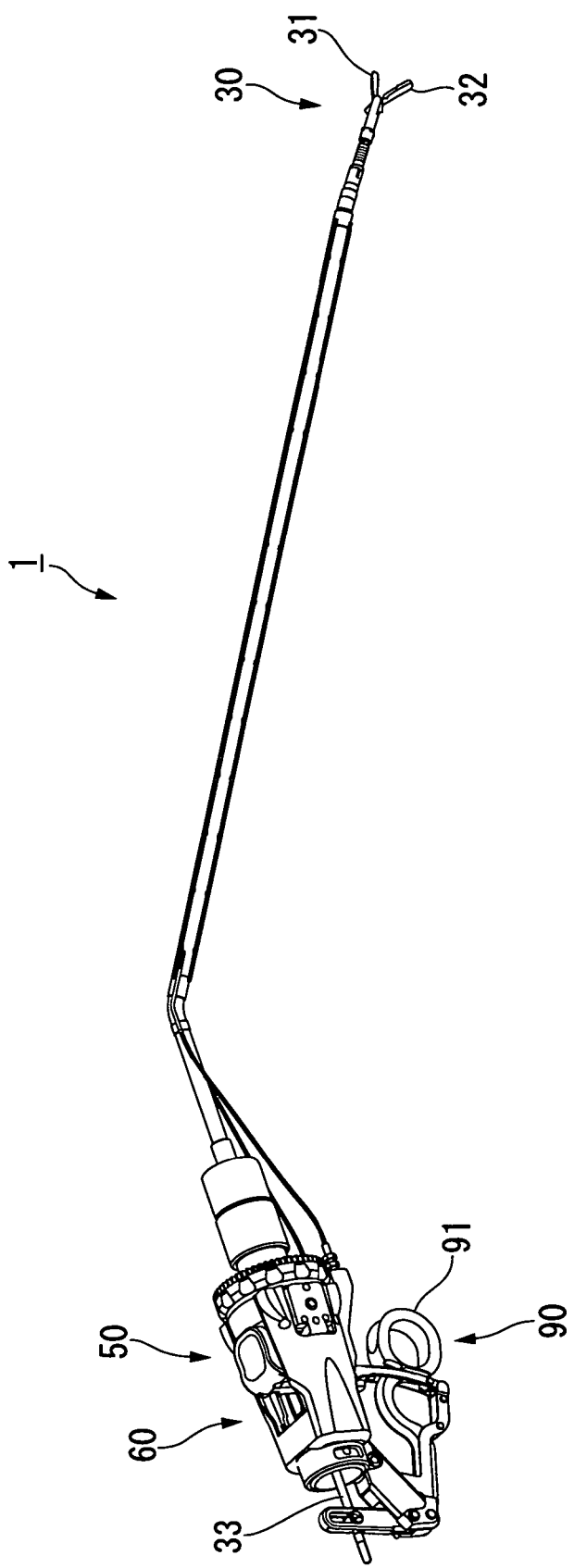
FIG. 2 is an overall view of the multi-degree-of-freedom forceps of the first embodiment of the present invention.

The treatment portion 30 has a well-known structure including a pair of openable and closable forceps pieces 31 and 32. As shown in FIGS. 1 and 2, an operating member 33 connected to the forceps pieces 31 and 32 is advanced and retreated by operating an opening and closing lever 91 provided at the operating portion 50. This enables the pair of forceps pieces 31 and 32 to be opened and closed. The operating member 33 extends in the longitudinal direction of the insertion portion 10.

As shown in FIG. 2, the operating portion 50 includes a first operating portion 60 for operating the second bending portion 12 and a second operating portion 90 for performing the opening and closing operation of the treatment portion 30.

Figure 4:
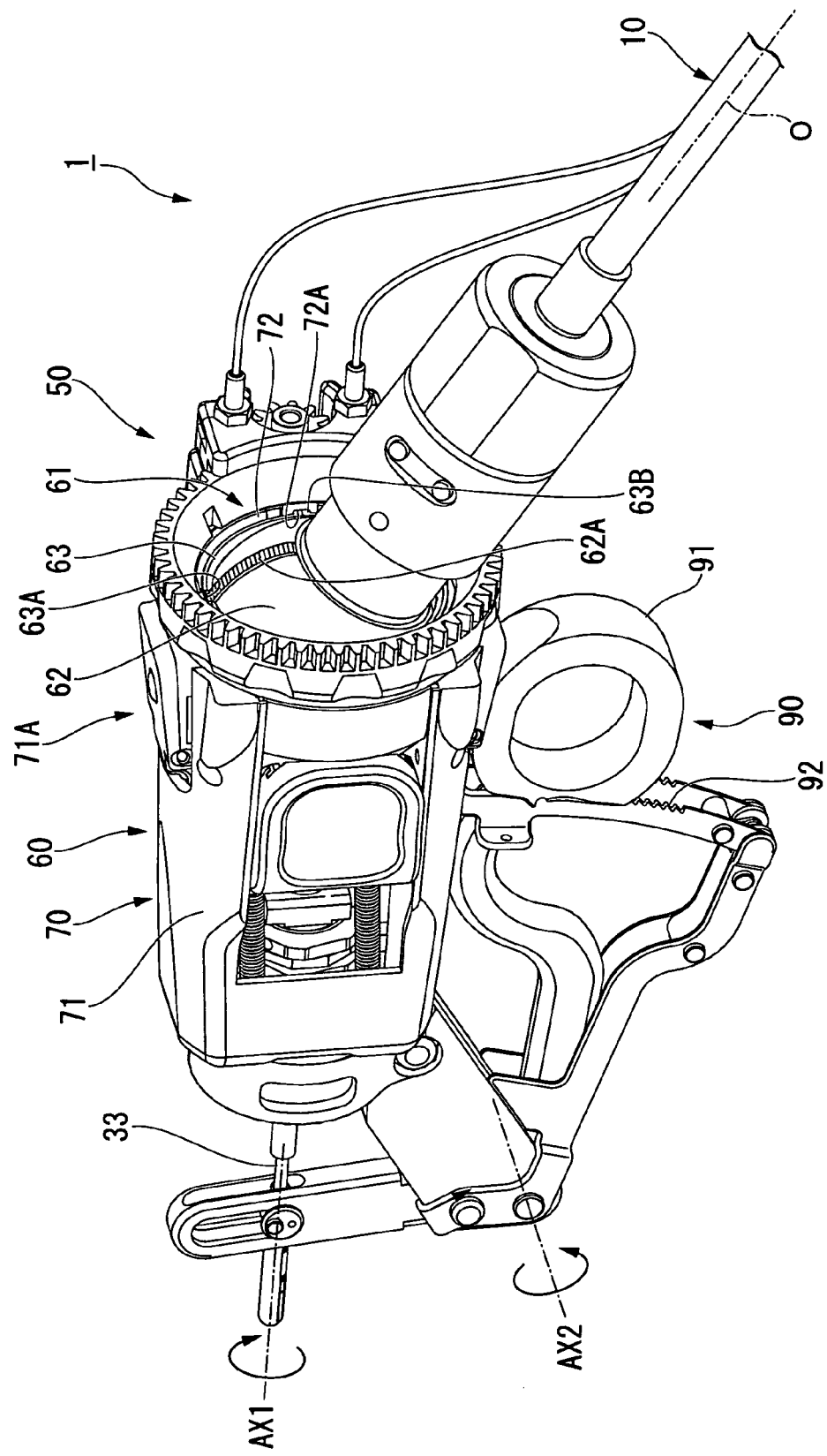
FIG. 4 is a perspective view of an operating portion of the multi-degree-of-freedom forceps.

FIG. 4 is a perspective view showing the operating portion 50. The first operating portion 60 includes a swivel joint portion (joint portion) 61 fixed to the insertion portion 10, and a handle portion 70 attached to the swivel joint portion 61.

FIG. 5A is a cross-sectional view of the first operating portion 60. As shown in FIGS. 4 and 5A, the swivel joint portion 61 has a first member 62 fixed to the distal end side of the second bending portion 12, and a second member 63 that has a second rotation axis O2 and is attached so as to cover a portion of the first member 62. Additionally, the second member 63 is attached so as to be rotatable around a first rotation axis O1 of the first member 62. The proximal end side of the first member 62 has a semispherical shape having a space therein. An outer peripheral surface of the first member 62 is formed with a circular-arc engaging protrusion (first engaging protrusion) 62A passing above a plane (the same plane as the cross-section of FIG. 5A) passing through the central axis of the insertion portion 10. The engaging protrusion 62A is formed in the shape of a sawtooth in which a plurality of ridges and valleys are alternately arranged in an extending direction. The second member 63 has an inner surface and an outer surface on a substantially spherical surface, and the inner surface thereof is formed with an engaging groove 63A with dimensions corresponding to the engaging protrusion 62A. The first member 62 and the second member 63 are assembled so that the engaging protrusion 62A is located within the engaging groove 63A. Therefore, the first member 62 and the second member 63 are engaged with each other so as to be relatively rotatable in the extending direction of the engaging protrusion 62A, with the center of the swivel joint portion 61 as a rotation center.

A regulating portion may be formed that regulates the operation direction of the handle body 71 (to be described below) relative to the insertion portion 10 in the same direction as the bending direction of the first bending portion 11 as the engaging groove 63A and the engaging protrusion 62A are engaged with each other. Additionally, the first bending portion 11 is provided at a distal end portion of the insertion portion 10 so as to be bendable according to the swinging operation of the handle body 71 relative to the insertion portion 10. In this case, an operator can grasp the bending direction intuitively. The engaging groove 63A and the engaging protrusion 62A may not be formed in the shape of a sawtooth, and the engaging groove 63A and the engaging protrusion 62A only have to be engaged with each other and regulate the operation direction. Additionally, an outer peripheral surface of the first member 62 may be formed with the engaging groove, and an inner surface of the second member 63 may be formed with the engaging protrusion.

Additionally, the insertion portion 10 extends along the longitudinal axis and has the swivel joint portion (joint portion) 61 at a proximal end portion thereof. The operating portion 50 has the handle body 71 that is coupled to the swivel joint portion 61 so as to be rotatable in a direction intersecting the longitudinal axis of the insertion portion 10 and is provided so as to be capable of swinging and operating relative to the insertion portion 10.

The handle portion 70 has the handle body 71 gripped by a user, and a receiving member 72 provided inside the handle body 71. The basic shape of the handle body 71 is a substantially hollow truncated conical shape whose cylindrical appearance expands gradually toward the distal end side, and a grip portion 71A is provided on the distal end side of the handle body 71. The grip portion 71A is provided around the oscillation center of the second bending portion 12 along the length direction of the handle portion 70 (so as to surround the operation center of the second bending portion 12). In the present embodiment, the grip portion 71A is arranged so as to wrap around the swivel joint portion 61. Additionally, the handle body 71 is attached so as to be rotatable around the second rotation axis O2 of the second member 63 orthogonal to the first rotation axis O1. Additionally, the grip portion 71A has a pair of grip surfaces, and the shape of the handle body 71 is not limited to the hollow truncated conical shape but only has to have a structure where the swivel joint portion 61 is arranged between a pair of grip surfaces which are gripped by the operator.

The receiving member 72 has a basic shape including an inner surface on a substantially spherical surface, and is attached so that the second member 63 of the swivel joint portion 61 is covered from the outside. The receiving member 72 is fixed to the handle body 71, and the proximal end side of the receiving member 72 is fixed to a proximal end portion 12A of the second bending portion 12.

Figure 5B:
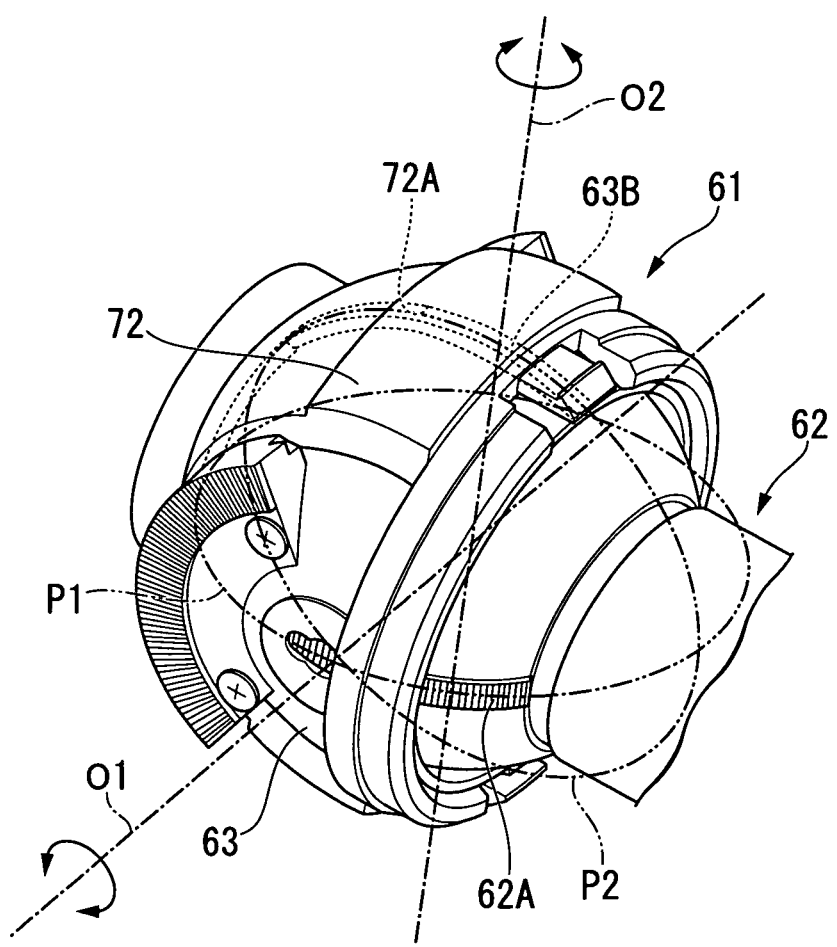
FIG. 5B is a perspective view showing a joint portion of the multi-degree-of-freedom forceps.

FIG. 5B is a perspective view of the swivel joint portion 61. As shown in FIG. 5B, an outer surface of the second member 63 is formed with the same engaging protrusion (second engaging protrusion) 63B as the first member 62, and an inner surface of the receiving member 72 is formed with an engaging groove 72A with dimensions corresponding to the engaging protrusion 63B. Since the second member 63 and the receiving member 72 are assembled so that the engaging protrusion 63B is located within the engaging groove 72A, the second member 63 and the receiving member 72 are relativity rotatable in an extending direction of the engaging protrusion 63B, with the center of the swivel joint portion 61 as a rotation center.

Figure 3:
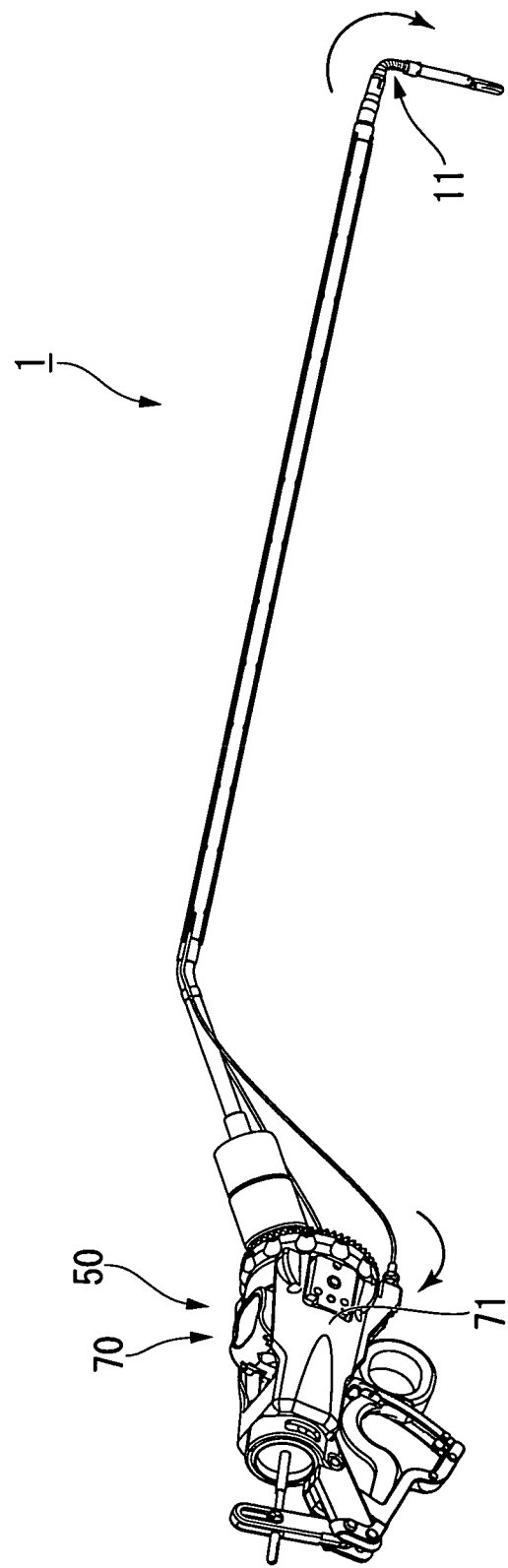
FIG. 3 is an overall view of the multi-degree-of-freedom forceps of the first embodiment of the present invention.

As shown in FIGS. 5A and 5B, a plane (a first plane including the engaging protrusion 62A on which a projection of a first claw member 155 is hooked) P1 defined by the engaging protrusion 62A of the first member 62, and a plane (second plane where oscillation is regulated by the fitting between the engaging groove 72A and the engaging protrusion 63B) P2 defined by the engaging protrusion 63B of the second member 63 are orthogonal to each other on a central axis OC of the second bending portion 12 in a state where the second bending portion 12 is made linear. By such assembling, the handle portion 70 is able to swing relative to the swivel joint portion 61, with the center of the swivel joint portion 61 as an operation center. If the handle body 71 of the handle portion 70 is swung, the receiving member 72 swings relative to the swivel joint portion 61, the proximal end portion 12A of the second bending portion 12 moves along with the receiving member 72, and the second bending portion 12 bends. As a result, as shown in FIG. 3, the operation direction of the handle body 71 relative to the insertion portion 10 is regulated in the same direction as the bending direction of the first bending portion 11, and the first bending portion 11 bends according to the operation direction of the handle body 71. In this case, the first claw member 155, the engaging protrusion 62A, the engaging groove 72A, and the engaging protrusion 63B function as a regulating portion.

As shown in FIG. 4, the second operating portion 90 has the opening and closing lever 91 attached so as to be rotatable around an axis AX2 relative to the handle portion 70. Since the operating member 33 connected to the forceps pieces 31 and 32 of the treatment portion 30 protrudes from the proximal end side of the first operating portion 60 and is connected to the opening and closing lever 91, the opening and closing lever 91 is operated, so that the operating member 33 can be advanced and retreated in the axis direction thereof and the pair of forceps pieces 31 and 32 can be opened and closed. Since the opening and closing lever 91 includes a ratchet 92, the opening angle of the forceps pieces 31 and 32 can be fixed to a desired degree by fixing the operation state of the opening and closing lever 91. Since the opening and closing lever 91 is rotatably attached to the handle portion 70 and the operating member 33 is arranged substantially coaxially with the axis O of the insertion portion 10, the second operating portion 90 is rotatable relative to the first operating portion 60, with an axis AX1 as a rotation center. Therefore, the positional relationship between the opening and closing lever 91 and each operation part of the first operating portion 60 to be described below can be freely adjusted.

Access Port and Pivot Portion

The multi-DOF forceps 1 is inserted through the access port attached to a patient and introduced into a body cavity. Additionally, since the multi-DOF forceps 1 is inserted through the access port in a state where pivot portions are attached to the insertion portion 10, the structure of the access port and the pivot portions will be described here.

An access port 100 has pivot portions 110 that supports the insertion portion 10 so as to be movable along the longitudinal axis and support the insertion portion 10 so as to be pivotally operable and that is mountable on a body wall.

Figure 6:
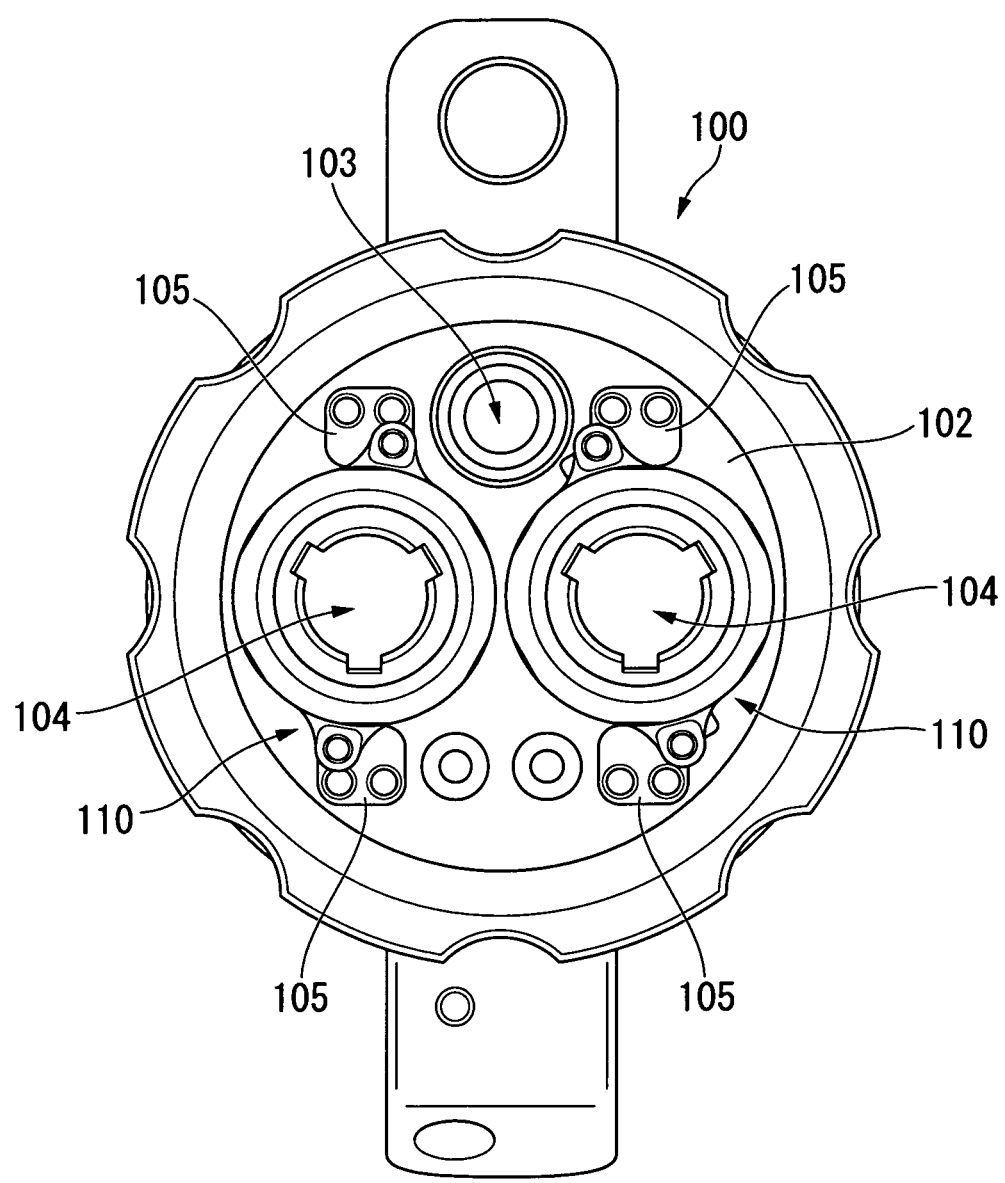
FIG. 6 is a front view of an access port to which pivot portions are attached.
Figure 7:
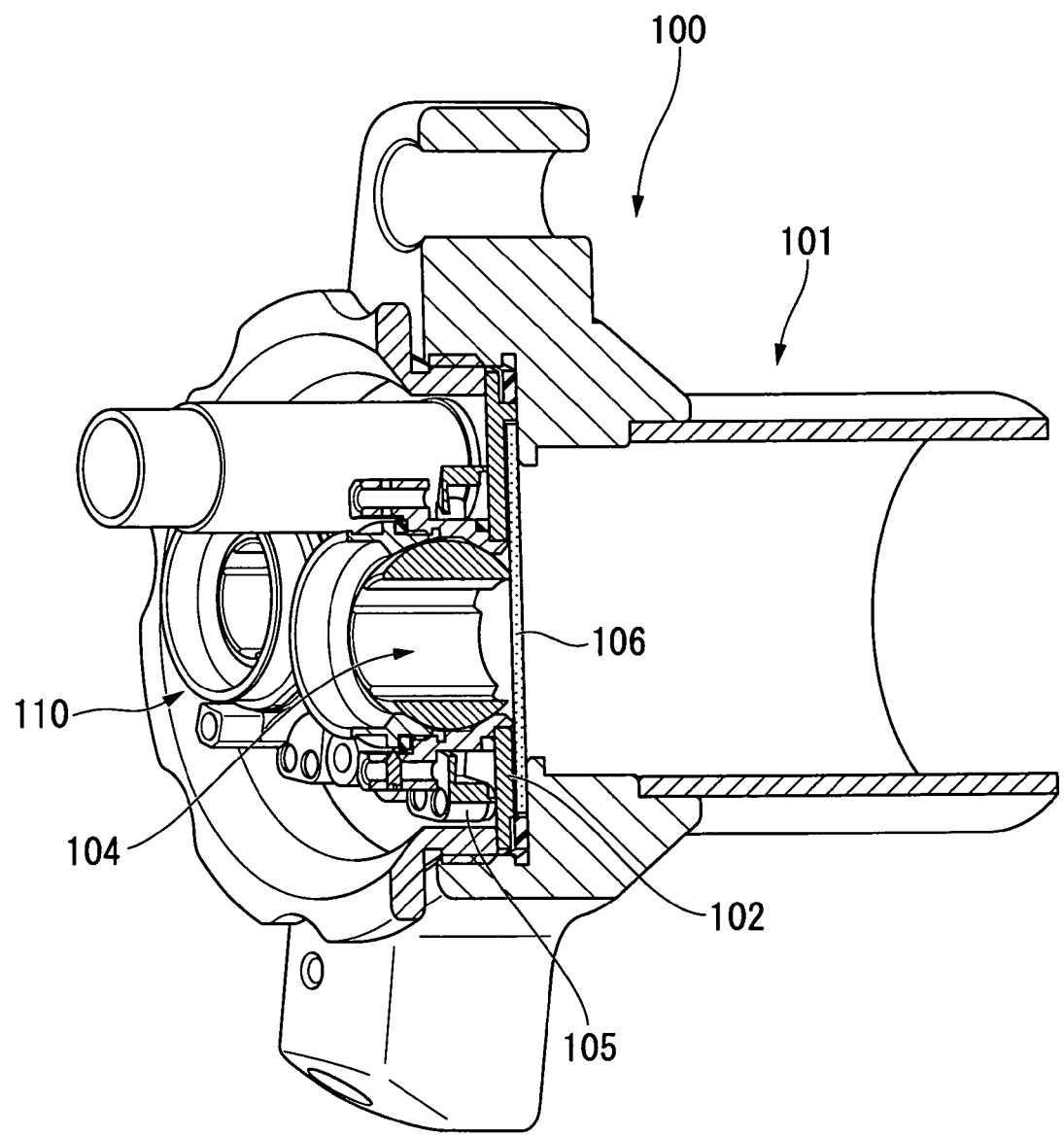
FIG. 7 is a cross-sectional view of the access port.

FIG. 6 is a front view of the access port 100 to which the pivot portions 110 are attached, and FIG. 7 is a cross-sectional view, in the axis direction of the access port 100, of the access port 100 to which the pivot portions 110 are attached. The access port 100 is installed in a hole formed in the body wall by incision or the like, or natural openings, such as the anus, and includes a tubular main body 101, and a port portion 102 to which the pivot portions are attached.

Figure 8A:
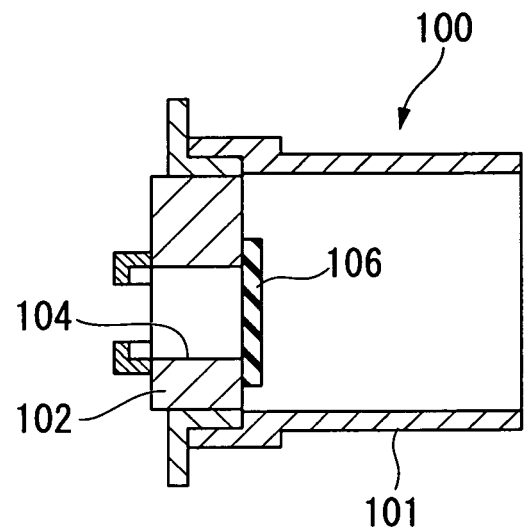
FIG. 8A is a schematic view showing a modified Example of the access port.
Figure 8B:
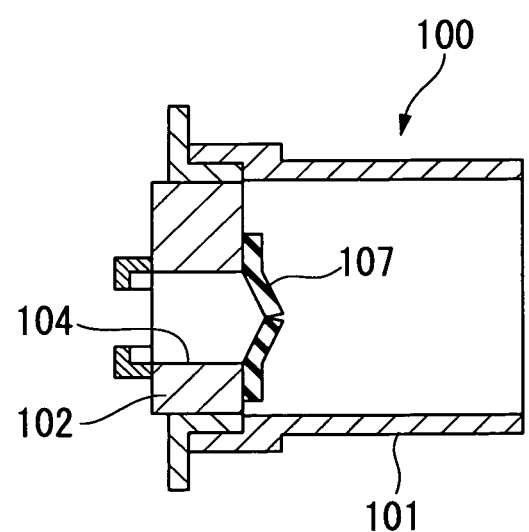
FIG. 8B is a schematic view showing a modified Example of the access port.

The port portion 102 is disk-shaped and is attached to one end portion side of a main body 101. The port portion 102 is formed with a total of three holes of one port 103 for an endoscope and two ports 104 for forceps. A pair of fixing members 105 for mounting a pivot portion 110 are arranged around each port 104 for forceps so as to face each other across the central axis of the port for forceps. As shown in FIG. 7, an airtight membrane (airtight portion) 106 made of rubber or the like with a slit is attached between the port portion 102 and the main body 101, and has a structure where airtightness at the port portion 102 side is maintained even in a state where there is not anything inserted through each port of the port portion 102. Instead of providing the airtight portion so as to be pinched between the port portion 102 and the main body 101, as schematically shown in FIG. 8A, airtight membranes 106 may be individually attached to respective ports, such as the ports 104 for forceps. Additionally, when the airtight portion is attached to each port, a valve 107 may be used instead of the airtight membrane as shown in FIG. 8B. As the valve 107, for example, a valve provided in a general trocar can be used.

Figure 9:
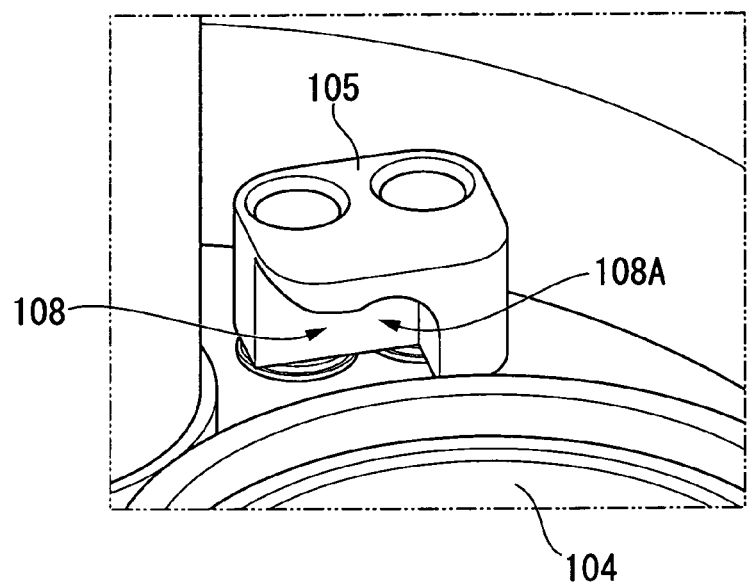
FIG. 9 is an enlarged view of a fixing member in the access port.

As shown in FIG. 9, a guide groove 108 to which a pin (to be described below) of the pivot portion 110 is locked is provided in each fixing member 105 so as to open toward the port 104 for forceps.

Figure 10:
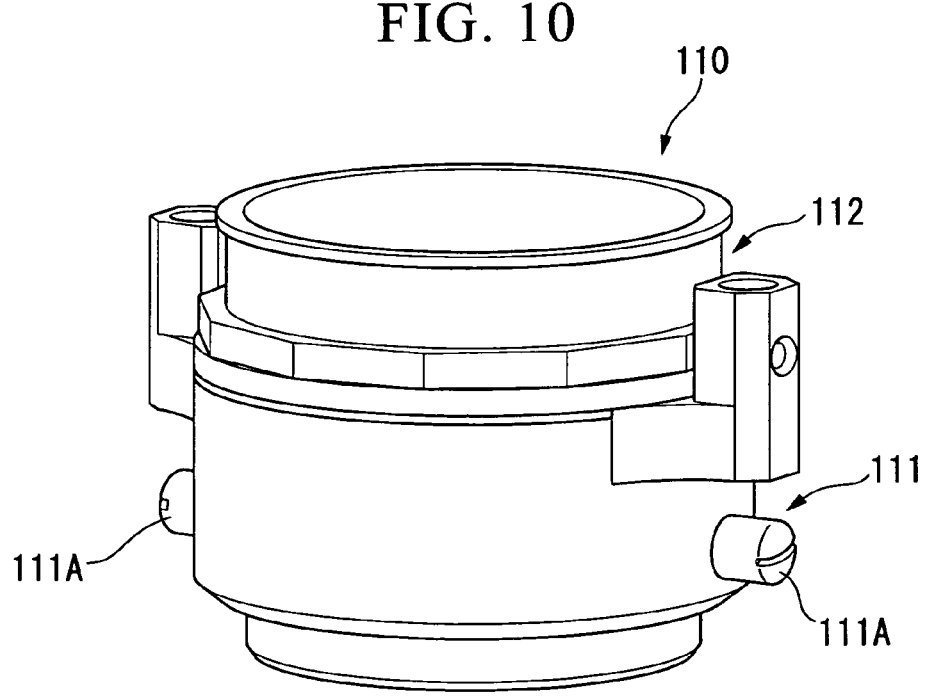
FIG. 10 is a perspective view of a pivot portion.
Figure 11:
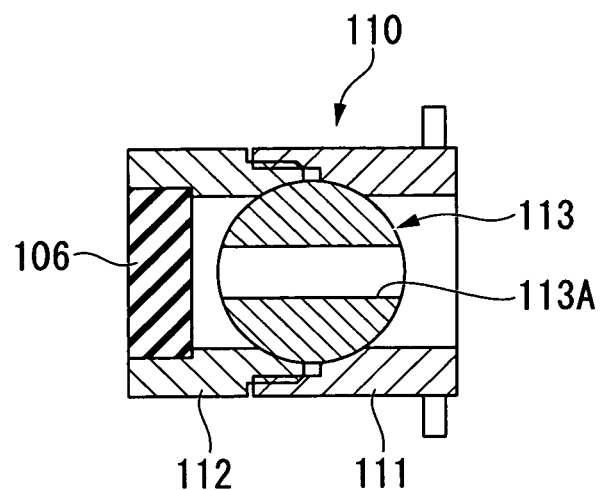
FIG. 11 is a schematic cross-sectional view of a pivot portion.

FIG. 10 is a perspective view of the pivot portion 110, and FIG. 11 is a schematic view showing the basic structure of the pivot portion 110. As shown in FIGS. 10 and 11, the pivot portion 110 includes a first cylindrical tubular portion 111 and a second cylindrical tubular portion 112, and a spherical portion 113 arranged at inner cavities of the first tubular portion 111 and the second tubular portion 112.

The spherical portion 113 is provided with a through hole 113A. The insertion portion 10 of the multi-DOF forceps 1 is inserted through the pivot portion 110 by passing through the through hole 113A. As the spherical portion 113 through which the insertion portion 10 is inserted slides so as to rotate relative to the first tubular portion 111 and the second tubular portion 112, the insertion portion 10 is capable of oscillating relative to the first tubular portion 111 and the second tubular portion 112 or the access port 100, with a central portion of the spherical portion 113 as an operation center, thereby performing a pivot operation.

The first tubular portion 111 and the second tubular portion 112 are integrally connected by screw fitting. By changing the screwing length of the first tubular portion 111 and the second tubular portion 112, the contact pressure between the inner surfaces of the first tubular portion 111 and the second tubular portion 112 and the outer surface of the spherical portion 113 can be adjusted to a constant range, and an operation feeling (weight) of the pivot operation can be adjusted to a desired state. For example, by setting a force required for the pivot operation to be greater than a force required for the oscillation of the handle body 71, the pivot operation can be kept from occurring inadvertently when bending the first bending portion 11. Additionally, since an optimal operation feeling of the pivot operation varies according to the specific configuration of the treatment portion 30, pivot portions whose weight is adjusted for each treatment portion may be prepared and separately used.

As shown in FIG. 10, a pair of pins 111A that are engaged with the guide grooves 108 of the access port 100 protrude from the outer peripheral surface of the first tubular portion 111. As shown in FIGS. 9 and 10, if the first tubular portion 111 is pressed against the port portion 102 and is rotated around an axis so that the pins 111A do not interfere with the fixing members 105, the pair of pins 111A enter the guide grooves 108, and the pivot portions 110 are mounted on the ports 104 for forceps. The width of a portion of each guide groove 108 that extends in the circumferential direction of the port 104 for forceps and is located ahead in the entering direction of the pin 111A is large. As the pin 111A enters the portion of the wide portion 108A, unintended falling of the pivot portion 110 is prevented. The pivot portion 110 removable from the access port 100 by rotating in a direction opposite to a direction when being mounted, and is attachable to and detachable from the access port 100.

Figure 12:
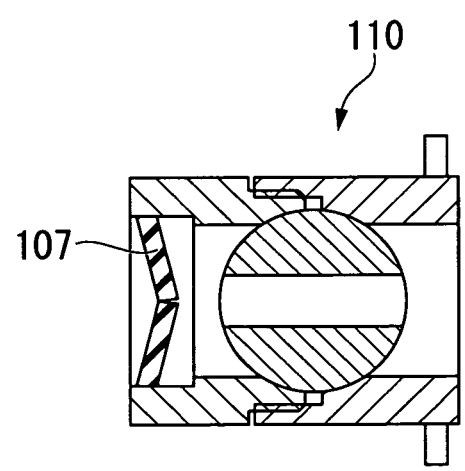
FIG. 12 is a schematic view showing a modified Example of the pivot portion.

As shown in FIG. 11, the airtight membrane 106 is attached to the proximal end side of the second tubular portion 112 located on the proximal end side when the pivot portion 110 is attached to the access port 100, similar to the access port. This maintains the airtight state of the access port even in a state where the insertion portion 10 is not inserted through the pivot portion 110. Instead of the airtight membrane 106, the valve 107 may be used as shown in FIG. 12, and this point is also the same as that of the access port. Additionally, the airtight membrane 106 only has to be provided in at least one of the first tubular portion 111 and the second tubular portion 112.

Since the detailed structure of the spherical portion 113 relates to the pivot locking mechanism that locks the pivot operation, this will be described below.

Locking Mechanism of Bending Operation and Pivot Operation and Switching Mechanism of Locked State Next, the mechanism of locking a bending operation and a pivot operation and the mechanism of switching locked states of these operations, which is one of the features of the multi-DOF forceps 1, will be described.

Figure 13A:
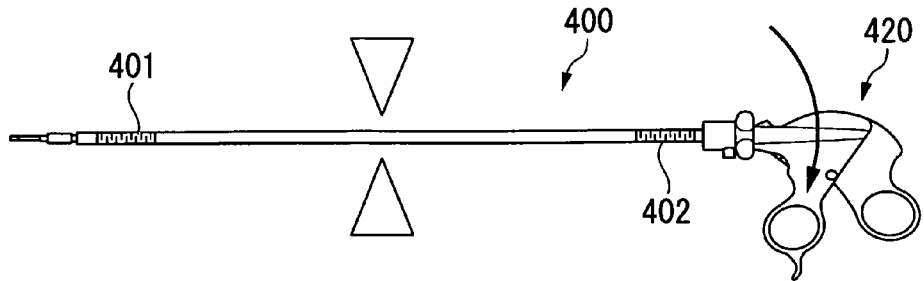
FIG. 13A is a view showing the operation when a multi-degree-of-freedom forceps of the related art is used.
Figure 13B:
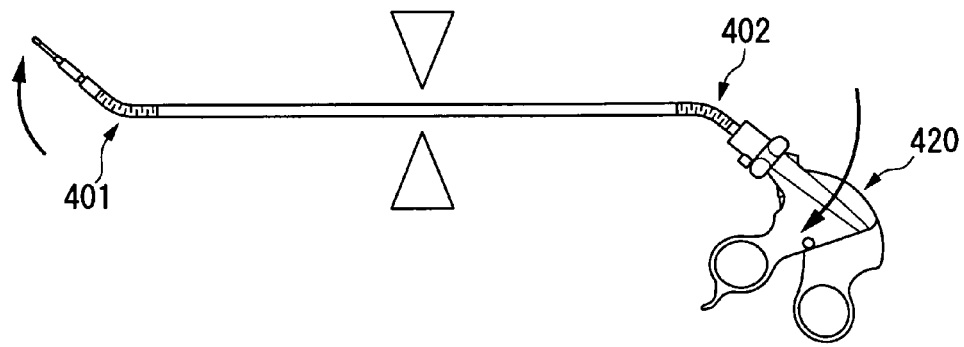
FIG. 13B is a view showing the operation when the multi-degree-of-freedom forceps of the related art is used.
Figure 13C:
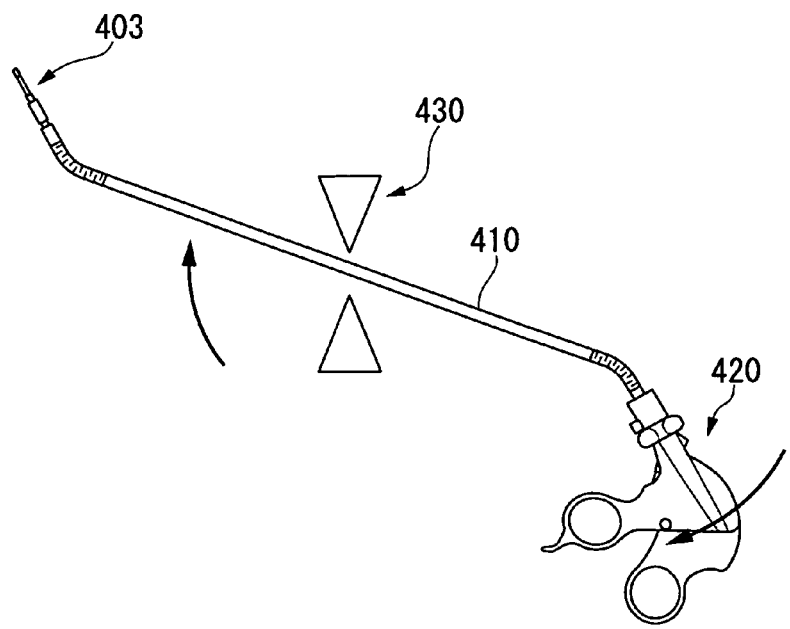
FIG. 13C is a view showing the operation when the multi-degree-of-freedom forceps of the related art is used.

FIGS. 13A to 13C are views describing the operation of a multi-DOF forceps of the related art. In a multi-DOF forceps 400 of the related art, if a second bending portion 402 is bent as shown in FIG. 13B by applying a force to an operating portion 420 from a state shown in FIG. 13A in order to bend a first bending portion 401, the pivot operation of an insertion portion 410 may occur with a fulcrum 430, such as the access port, as an operation center as shown in FIG. 13C, along with the bending operation of the second bending portion 402. This causes movement of the treatment portion 403 to an unintended position during a procedure.

One of the causes is that, since the operating portion 420 gripped by the user is located closer to the proximal end side than an intermediate portion (hereinafter simply referred to as "operation center") of the second bending portion 402 that is a substantial operation center of the second bending portion 402, a force for bending the second bending portion 402 acts also as a moment that pivotally operates the insertion portion 410.

Figure 14:
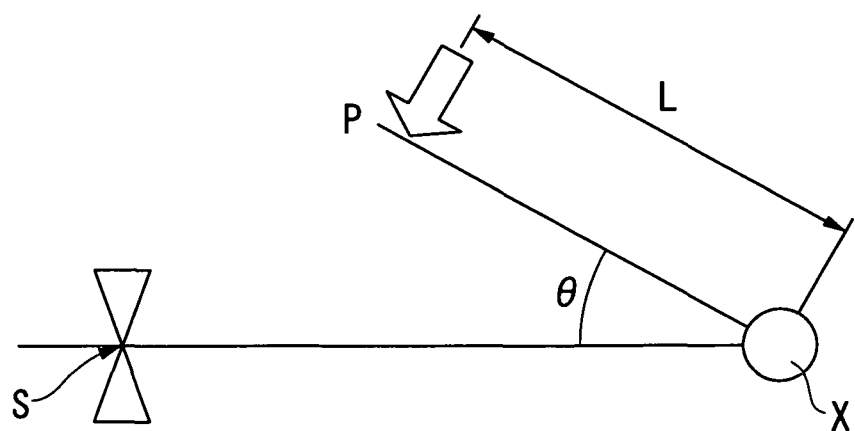
FIG. 14 is a view for describing a force that acts when the multi-degree-of-freedom forceps is used.

Additionally, even when the user does not apply a force to the operating portion intentionally, the first bending portion may bend along with the advance or retreat operation or pivot operation of the insertion portion. FIG. 14 is a schematic view describing this case, and shows a position where the user applies an operation force as a force point P, the operation center as X, and the access port as a fulcrum S. In FIG. 14, if the distance between the fulcrum S and the operation center X changes or the fulcrum S moves relative to the operation center X while keeping the distance from the operation center X constant, a torque around the operation center X is generated according to the distance L between the force point P and the operation center X. In the operation of the multi-DOF forceps, the operation of advancing and retreating the insertion portion relative to the pivot portion is the operation of changing the distance between the fulcrum S and the operation center X, and the pivot operation is the operation of moving the fulcrum S relative to the operation center X while keeping the distance from the operation center X constant. Accordingly, along with these operations, the above-described torque is generated and an unintended operation of the first bending portion is generated.

Figure 15:
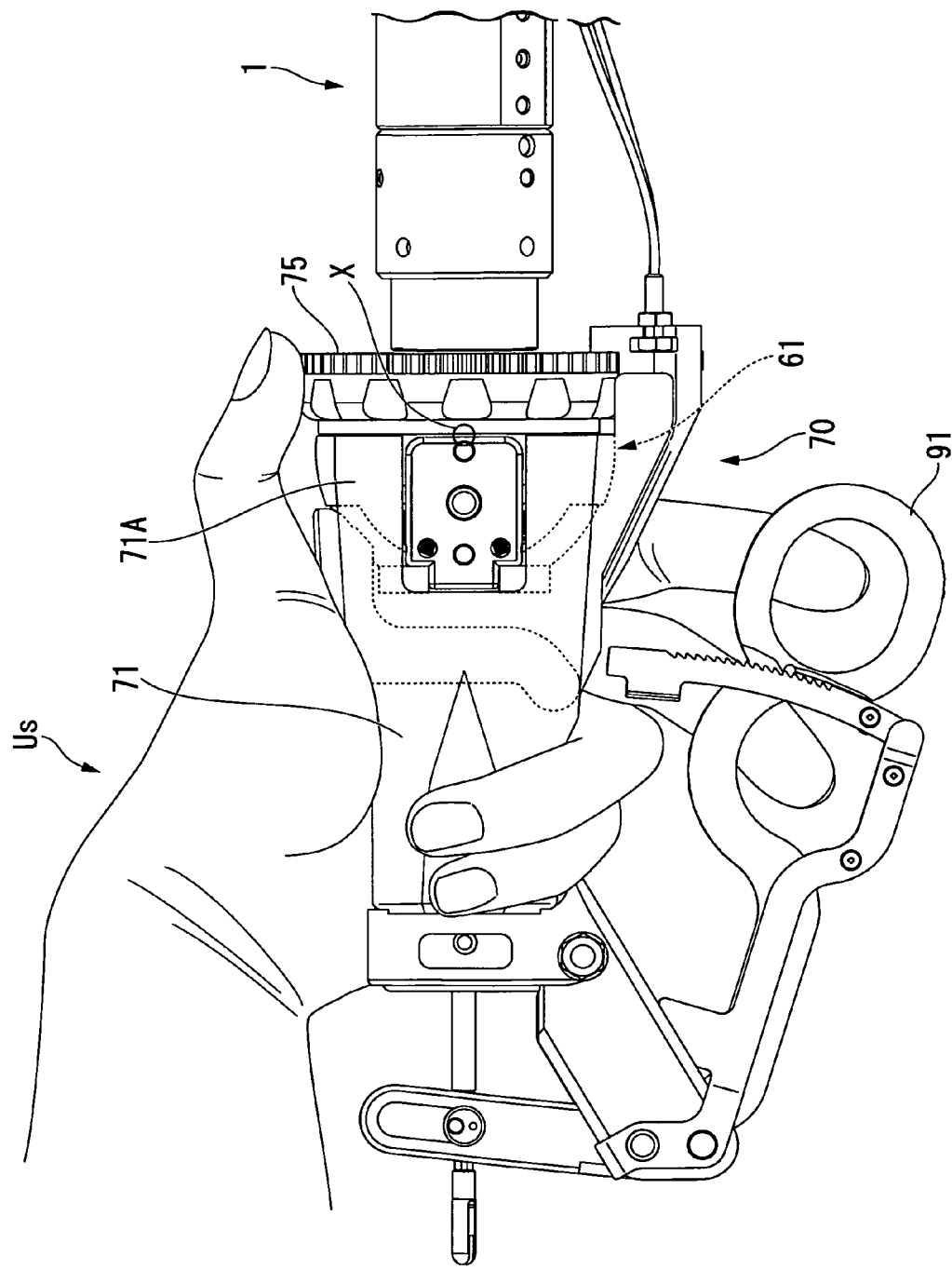
FIG. 15 is a view showing a state where a user grips the operating portion of the multi-degree-of-freedom forceps.

In the multi-DOF forceps 1 of the present embodiment, as shown in FIG. 15, the user grips the handle body 71 of the handle portion 70 and operates a dial 75 (to be described below) and the opening and closing lever 91 with arbitrary fingers. At this time, a hand or fingers of the user Us who grips a grip portion 71A of the handle body 71 are arranged so as to wrap around the swivel joint portion 61 that is also the operation center of the handle portion 70 including the operation center X. In such a gripped state, the distance between the force point P and the operation center X becomes significantly shorter than the multi-DOF forceps of the related art. As a result, the above-described moment generated when a force is applied to the handle portion 70 so as to bend the second bending portion 12 becomes significantly small, and the above-described torque also becomes small. Accordingly, since the grip portion 71A is arranged around the operation center X, the user can easily separate the bending operation of the first bending portion 11 from the pivot operation of the insertion portion to operate the multi-DOF forceps, without advanced skill.

Here, in order to completely eliminate the above-described torque, it is required to make the distance between the fulcrum S and the operation center X zero, but this is not practical in terms of the configuration of the multi-DOF forceps. Thus, the bending locking mechanism and the pivot locking mechanism that lock the bending operation and the pivot operation are provided in the multi-DOF forceps 1 in order to more reliably separate the pivot operation from the advance or retreat operation of the insertion portion and bending operation.

The bending locking mechanism 150 enables fixation of the rotation of the insertion portion 10 in the direction intersecting the longitudinal axis of the insertion portion 10 relative to the handle body 71, and release of this fixation.

The pivot locking mechanism 160 enables fixation of the pivot operation of the insertion portion 10 relative to the pivot portion 110 to be described below and the movement of the insertion portion in the direction along the longitudinal axis, and release of this fixation.

Bending Locking Mechanism

Figure 16:
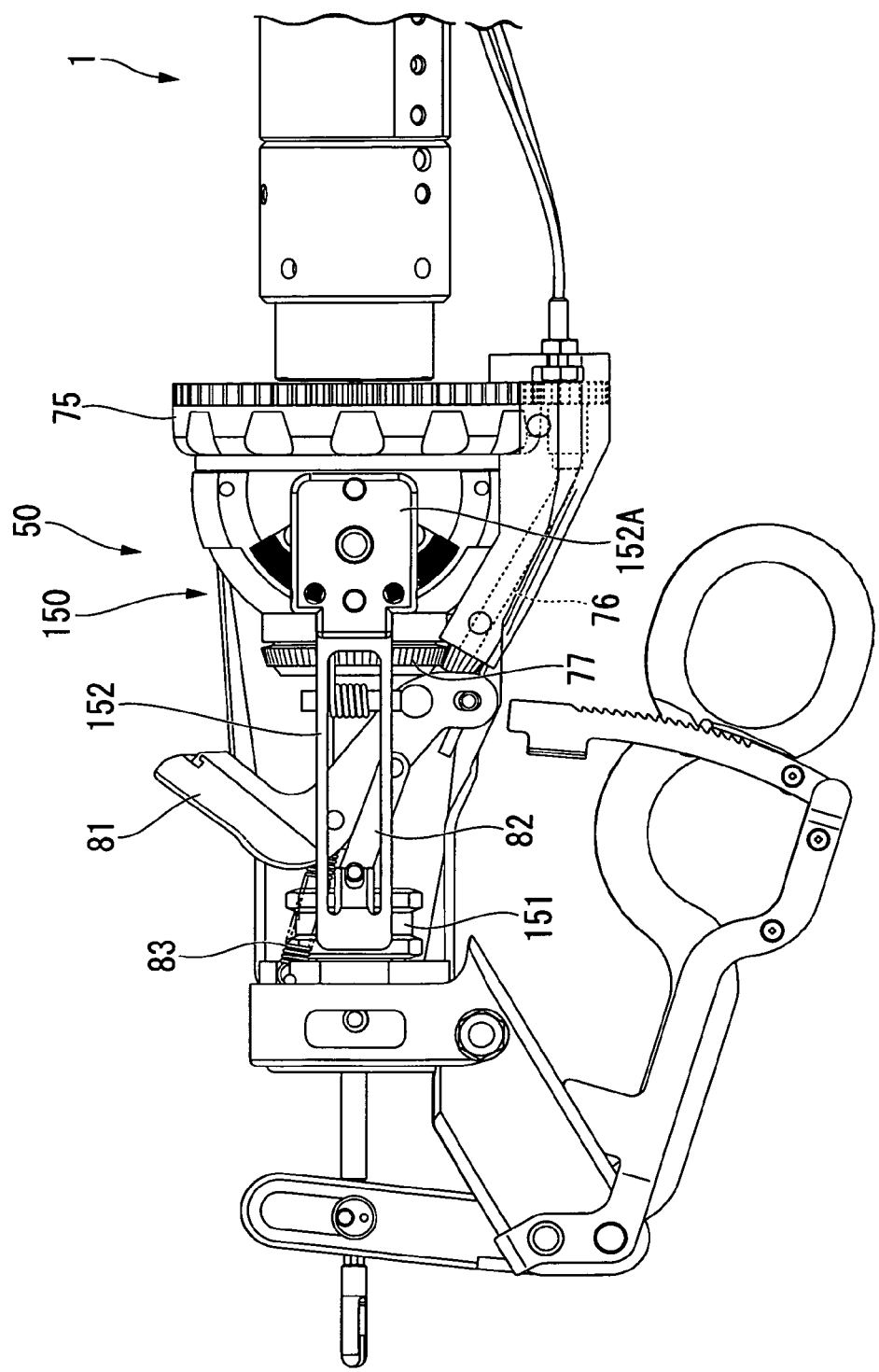
FIG. 16 is a view showing the operating portion excluding a handle body.
Figure 17:
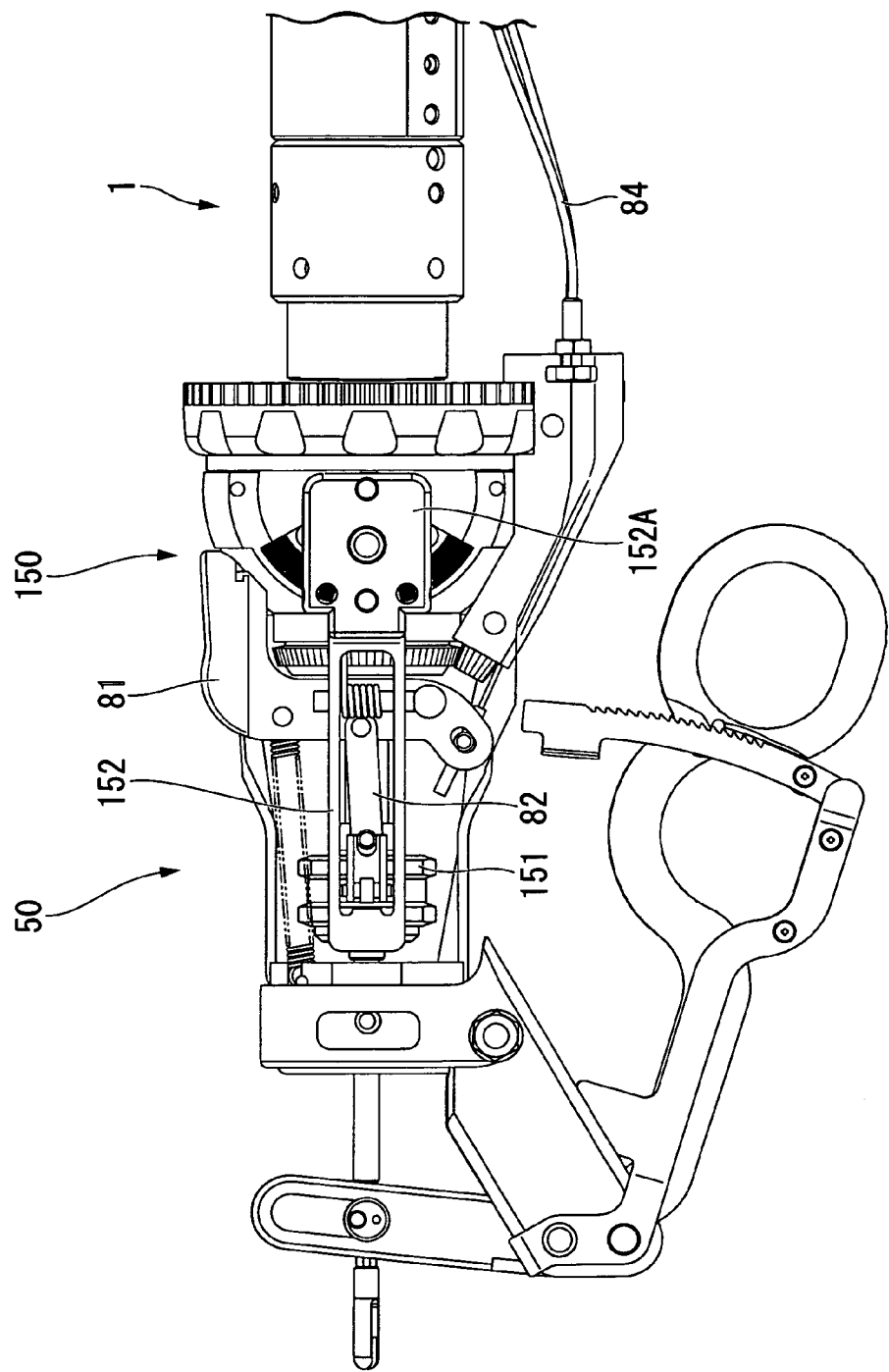
FIG. 17 is a view showing the operating portion excluding the handle body.
Figure 18:
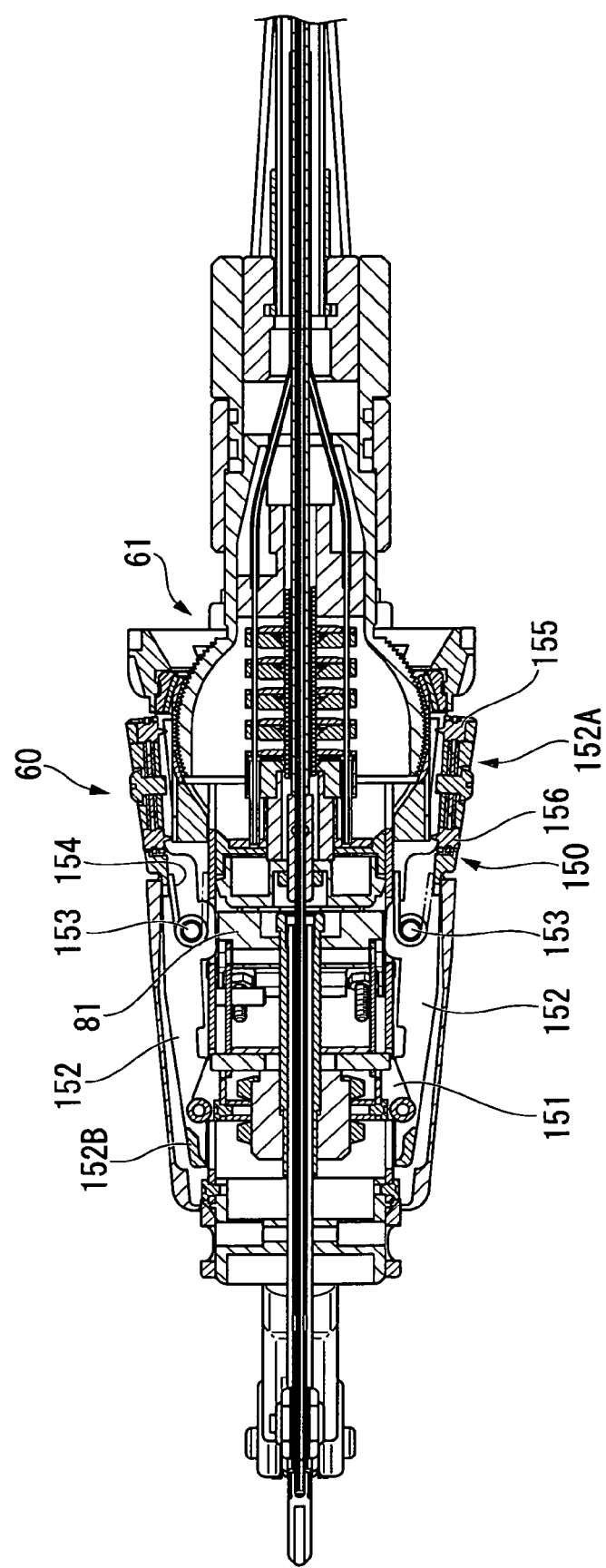
FIG. 18 is a cross-sectional view of the first operating portion.

FIGS. 16 and 17 are views showing the operating portion 50 excluding the handle body 71. FIG. 18 is a cross-sectional view of the first operating portion 60, and shows a state different from FIG. 5A. The bending locking mechanism 150 includes a movable body 151 and a pair of locking members 152 that are arranged within the handle body 71.

The operation and release of the bending locking mechanism 150 are performed by the locking lever (switching operating portion) 81 attached to the first operating portion 60. That is, the locking lever 81 performs switching between a state where the fixation by the bending locking mechanism 150 is released and the fixation by the pivot locking mechanism 160 is performed, and a state where the fixation by the bending locking mechanism 150 is performed and the fixation by the pivot locking mechanism 160 is released. The locking lever 81 may perform switching to a state where the fixation by the bending locking mechanism 150 is released and the fixation by the pivot locking mechanism 160 is released.

The locking lever 81 and the movable body 151 are connected by a link 82. As shown in FIG. 16, the movable body 151 moves to the proximal end side if the locking lever 81 is distal endped to the proximal end side, and the movable body 151 moves to the distal end side if the locking lever is pulled up to the distal end side.

As shown in FIG. 16, the locking lever 81 is arranged between the pair of locking members 152, and as shown in FIG. 18, respective intermediate portions of the pair of locking members 152 are fixed to the first operating portion 60 by a pivot shaft 153. Accordingly, each locking member 152 is rotatable around the pivot shaft 153. The first claw member 155 and the second claw member 156 that engage the swivel joint portion 61 are provided at a distal end portion 152A of each locking member 152 so as to protrude toward the swivel joint portion 61. A proximal end portion 152B of each locking member 152 is located closer to the proximal end side than the movable body 151. Additionally, a torsion spring 154 is attached to each pivot shaft 153. The pair of locking members 152 are biased by the torsion springs 154 so that the distance between the distal end portions 152A becomes larger than the distance between the proximal end portions 152B.

The locking member 152 may be provided so that the distal end portion of the locking member 152 of the bending locking mechanism 150 is movable from a position apart from the swivel joint portion 61 to a position where the locking member is locked to the swivel joint portion 61. Additionally, as the distal end portion of the locking member 152 is locked to the swivel joint portion 61, the locking member 152 may fix the handle body 71 to the insertion portion 10 in the direction intersecting the longitudinal axis of the insertion portion 10.

The operation of the bending locking mechanism 150 will be described.

If the locking lever 81 is distal endped toward the proximal end side, the movable body 151 moves to the proximal end side, and as shown in FIG. 5A, enters between two proximal end portions 152B of the pair of locking members 152. Therefore, the two proximal end portions 152B are moved by the pair of locking members 152 so that the distance between the proximal end portions 152B increases. Each locking member 152 rotates around the pivot shaft 153, and the distal end portion 152A approaches the swivel joint portion 61. The first claw member 155 provided at the distal end portion 152A bites the engaging protrusion 62A of the first member 62 exposed in a portion from between the first claw member and the second member 63 in the swivel joint portion 61, and is locked so that the first member 62 cannot rotate relative to the handle body 71. On the other hand, the second claw member 156 bites a sawtooth-shaped locking protrusion 63C provided parallel to the engaging protrusion 63B on the outer surface of the second member 63, and is locked so that the second member 63 cannot rotate relative to the handle body 71. Therefore, the swivel joint portion 61 is completely locked to the handle portion 70, and the bending operation is fixed so that the state of the first bending portion 11 and the second bending portion 12 do not change.

Whether the first claw member 155 and the second claw member 156 approach any of ridges and valleys of the sawtooth shape of the engaging protrusion 62A and the locking protrusion 63C varies depending on the bending state of the second bending portion 12 or the like. As shown in FIG. 5A, a plate spring 157 is oscillatably arranged in connection regions between the locking members 152, and the first claw member 155 and the second claw member 156, and the elastic force of the plate spring 157 acts so as to suppress position changes in the respective claw members 155 and 156 caused by an approaching part. As a result, irrespective of the bending state of the second bending portion 12, eventually, the respective claw members 155 and 156 reliably bite the swivel joint portion 61 and the bending operation is locked.

The operating state of the bending locking mechanism 150 is maintained by a spring 83 that is connected to the locking lever 81 to bias the locking lever 81 to the proximal end side, and a frictional force generated between the movable body 151, which has entered between the proximal end portions 152B, and the proximal end portions 152B even if the user removes user's hand from the locking lever 81. Additionally, the distal end portion 152A of each locking member 152 is exposed onto the outer surface of the handle body from a cutout provided in the handle body 71. Accordingly, as the user presses the distal end portions 152A to engage the respective claw members 155 and 156 with the swivel joint portion 61 even in a state where the locking lever 81 is pulled up, it is possible to temporarily lock the bending operation.

If the user pulls up the locking lever 81, the movable body 151 separates from the proximal end portions 152B of the locking members 152, and is brought into non-contact with the proximal end portions 152B. Therefore, the distal end portions 152A of the pair of locking members 152 separate from the swivel joint portion 61 by the biasing forces of the torsion springs 154, and the swivel joint portion 61 is rotatable relative to the handle portion 70.

Pivot Locking Mechanism

Figure 19:
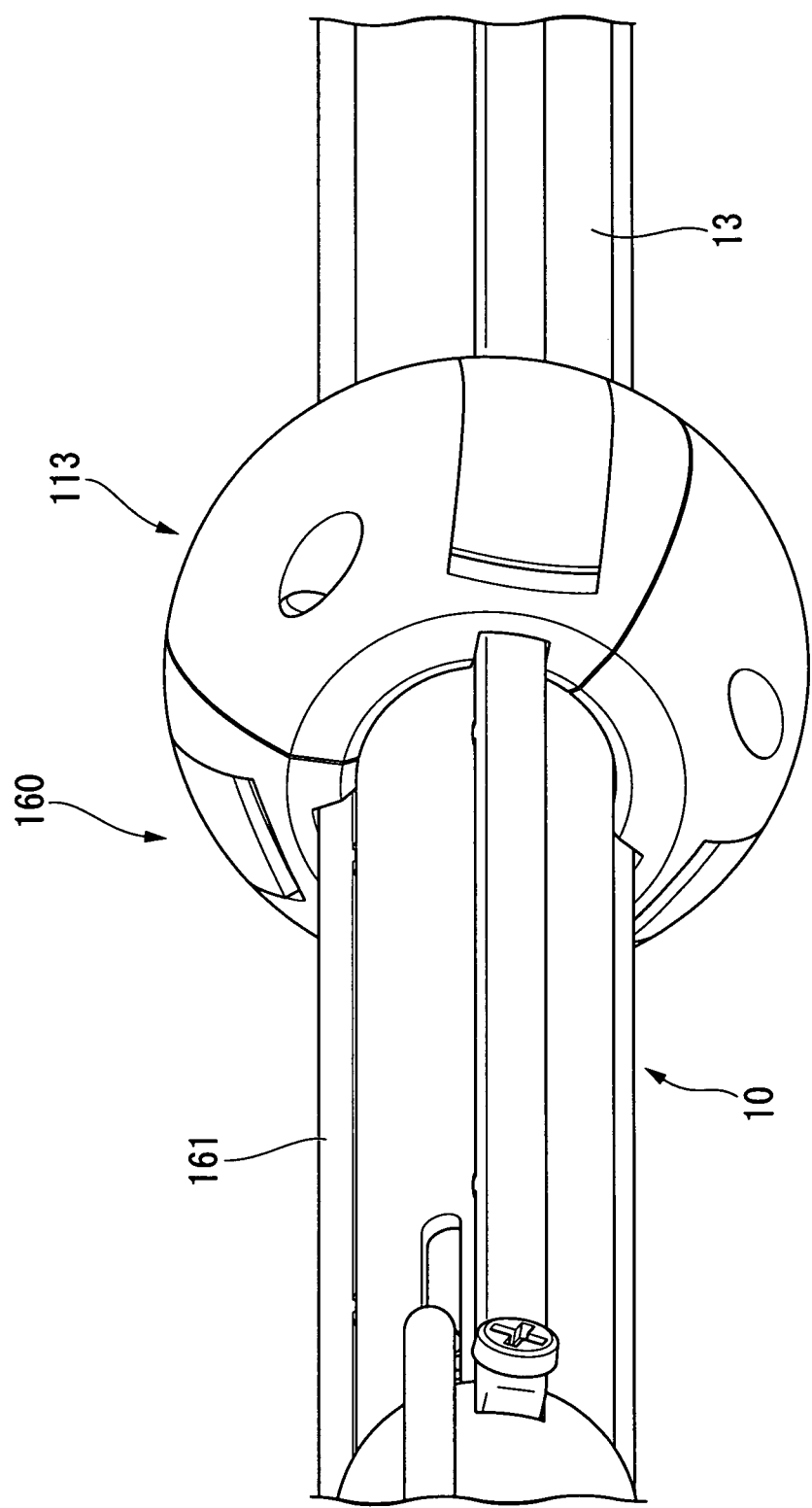
FIG. 19 is an enlarged perspective view of a pivot locking mechanism.

FIG. 19 is an enlarged perspective view showing the pivot locking mechanism 160. The pivot locking mechanism 160 is configured by a plurality of rail members 161 provided along the longitudinal direction of the insertion portion 10, and the spherical portion 113 of the pivot portion 110.

Figure 20:
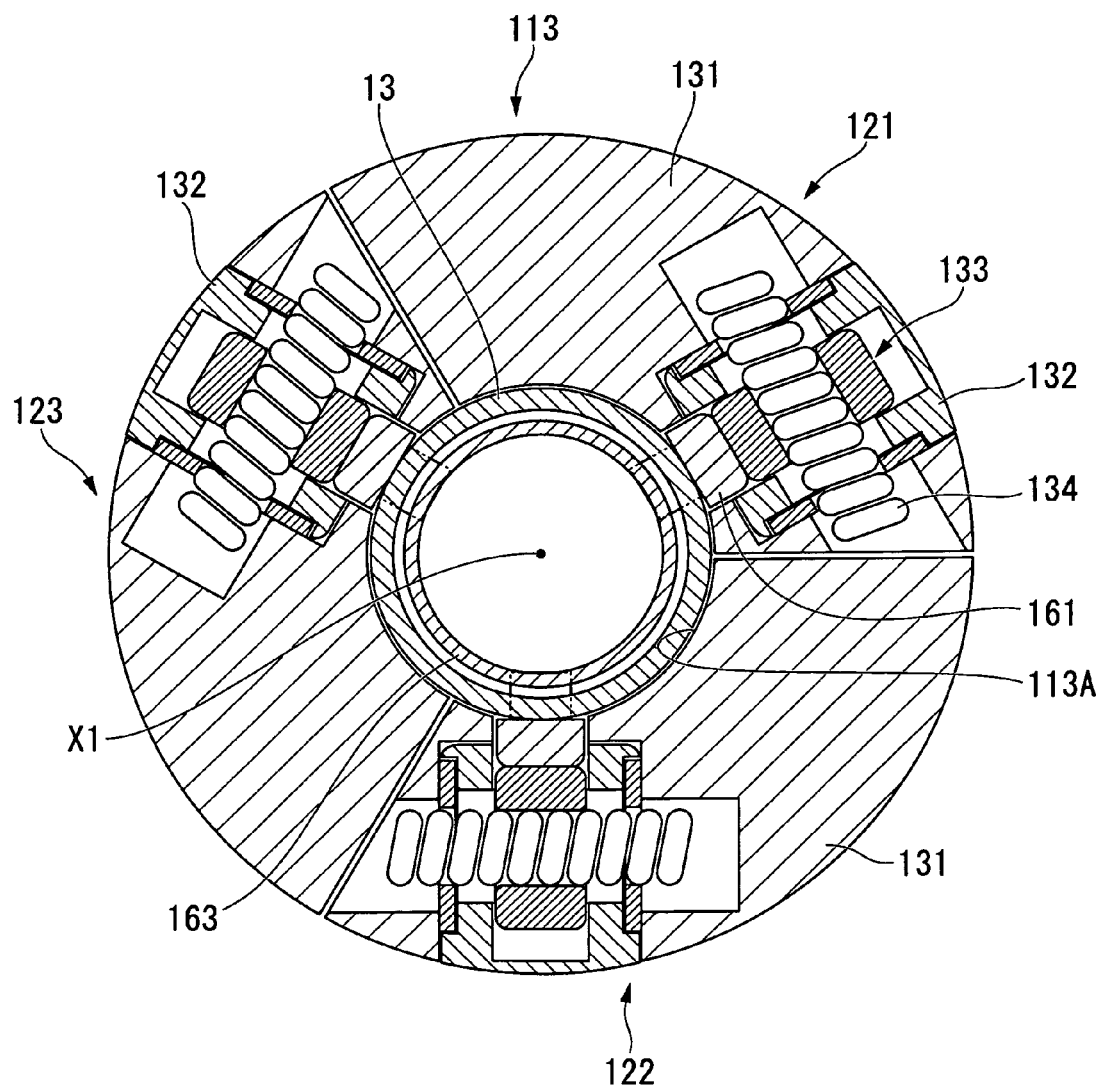
FIG. 20 is a cross-sectional view of a spherical portion.

FIG. 20 is a cross-sectional view of the spherical portion 113 in a cross-section orthogonal to the through hole 113A. The spherical portion 113 includes a first region 121, a second region 122, and a third region 123 that are divided at every central angle of 120 degrees around a central axis X1 of the through hole 113A. Each of the regions 121, 122, and 123 has a relatively large base member 131 and a relatively small movable member 132, and a bearing 133 is attached to each movable member 132. The rotation plane of each bearing 133 passes through the central axis X1 and is parallel to the central axis X1. A rotating shaft 134 of each bearing 133 is formed from a coil, and has flexibility such that the rotating shaft flexes to a certain degree in the longitudinal direction.

Additionally, the movable members 132 of the pivot locking mechanism 160 may be provided so as to be movable from a position apart from the pivot portion 110 to a position where the pivot portion 110 is pressed. Additionally, the fixation by the pivot locking mechanism 160 may be performed by the movable members 132 pressing the pivot portion 110.

Figure 21:
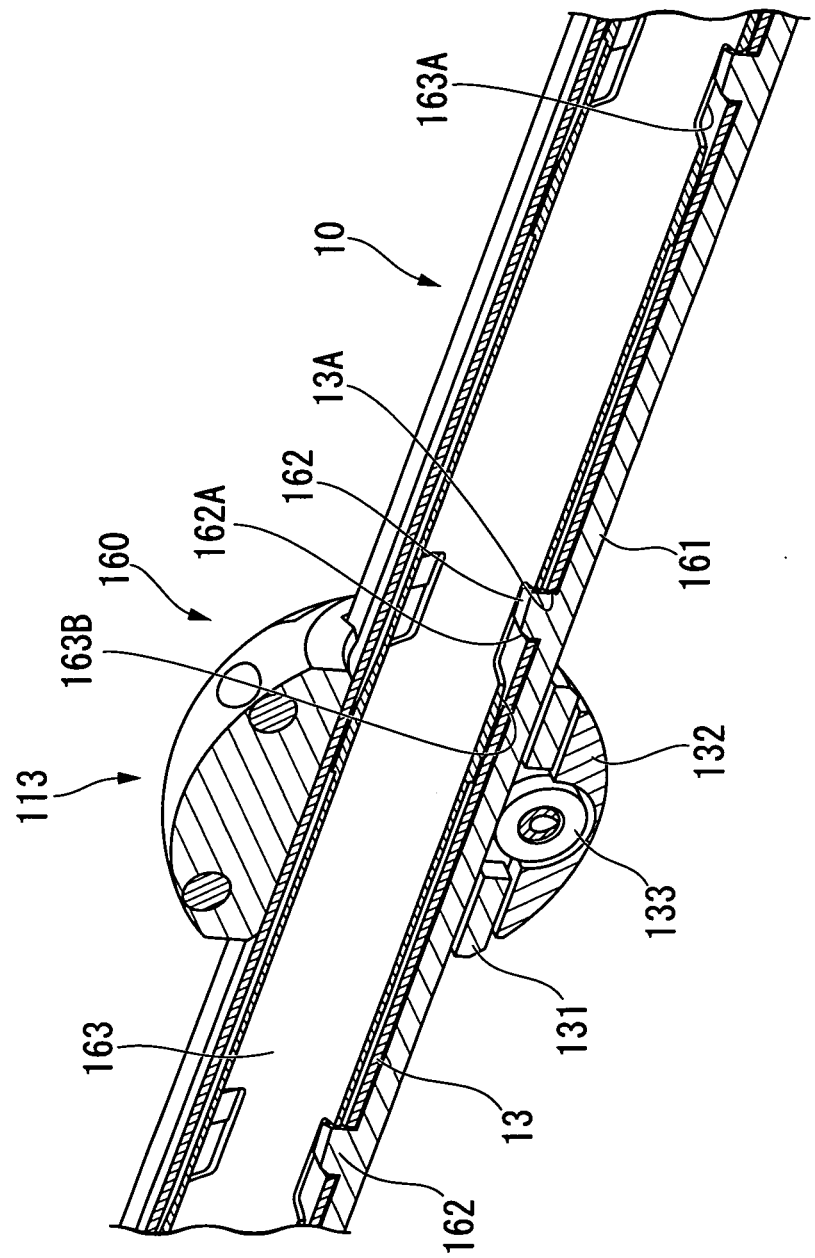
FIG. 21 is a cross-sectional view of the pivot locking mechanism.

Three rail members 161 are attached so as to be parallel to the axis of the insertion portion 10 and 120 degrees apart in the circumferential direction. FIG. 21 is a cross-sectional view in a cross-section of the pivot locking mechanism 160 parallel to the axis of the insertion portion. As shown in FIG. 21, a plurality of legs 162 that protrude toward the insertion portion 10 are provided at intervals in each rail member 161. The dimension of each leg 162 in the longitudinal direction of the rail member 161 becomes gradually shorter when approaching a projection end, and an inclination surface 162A is formed on the distal end side of each leg 162.

Each leg 162 enters the insertion portion 10 through a hole 13A formed in an outer pipe 13 of the insertion portion 10. A locking pipe 163 for making each rail member 161 approach and separate from the outer peripheral surface of the outer pipe 13 is inserted into the outer pipe 13. The outer surface of the locking pipe 163 is formed with a sliding hole 163A corresponding to each leg 162. Each leg 162 enters an inner cavity of the locking pipe 163 through the hole 13A of the outer pipe 13 and the sliding hole 163A of the locking pipe 163. A portion of the outer peripheral surface of the locking pipe 163 is formed so as to become gradually thin toward the distal end side of the sliding hole 163A. An inclination surface 163B is formed on the distal end side of the sliding hole 163A.

The locking pipe 163 and the locking lever 81 of the operating portion 50 are connected by an operating member 84 (refer to FIG. 17), such as a wire. If the locking lever 81 is distal endped to the proximal end side, the operating member 84 is pushed out and the locking pipe 163 moves (advances) to the distal end side, and if the locking lever 81 is pulled up, the operating member 84 is towed and the locking pipe 163 moves (retreats) to the proximal end side.

The operation of the pivot locking mechanism 160 will be described.

In a state where the locking lever 81 is distal endped to the proximal end side, as shown in FIGS. 20 and 21, the insertion portion 10 and the spherical portion 113 only come into contact with each other with the bearings 133 and the rail members 161. In this state, the insertion portion 10 can be easily and pivotally operated, and the advance-retreat resistance of the insertion portion 10 is reduced by the rotation of the bearings 133, and the insertion portion 10 can be smoothly advanced and retreated relative to the spherical portion 113.

If the locking lever 81 is pulled up, the locking pipe 163 retreats gradually and eventually the inclination surface 163B of the locking pipe 163 and the inclination surfaces 162A of the legs 162 of the rail members 161 come into contact with each other. Moreover, if the locking pipe 163 retreats, the rail members 161 are gradually pushed up by the locking pipe 163, and the rail members 161 begin to separate from the outer peripheral surface of the outer pipe 13.

Figure 22:
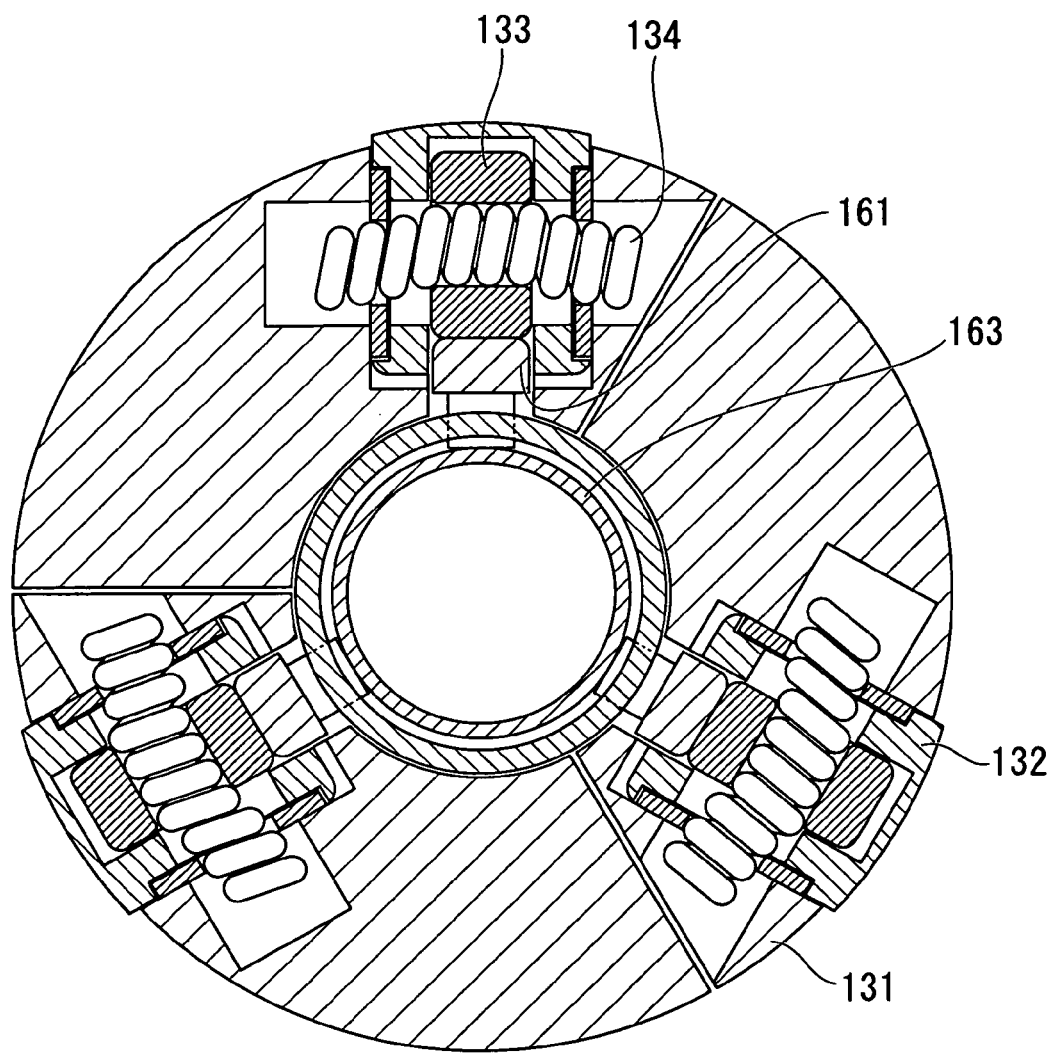
FIG. 22 is a cross-sectional view of the spherical portion when the pivot locking mechanism is operated.

The rail members 161 separating from the outer pipe 13 first press the bearings 133 of the respective regions 121, 122, and 123. As shown in FIG. 22, each bearing 133 is pushed up to the rail member 161 while flexing the rotating shaft 134. After the rotating shaft 134 is flexed by a certain amount, the movable members 132 are pushed up together with the bearings 133. As a result, each movable member 132 protrudes from the base member 131, the contact pressure between the first and second tubular portions 111 and 112 and the spherical portion 113 of the pivot portion 110 increases at the portion of the movable member 132, and a force required for the pivot operation increases. Even in this state, the advance-retreat operation of the insertion portion 10 can be performed with a comparatively small force by the bearings 133.

Figure 23:
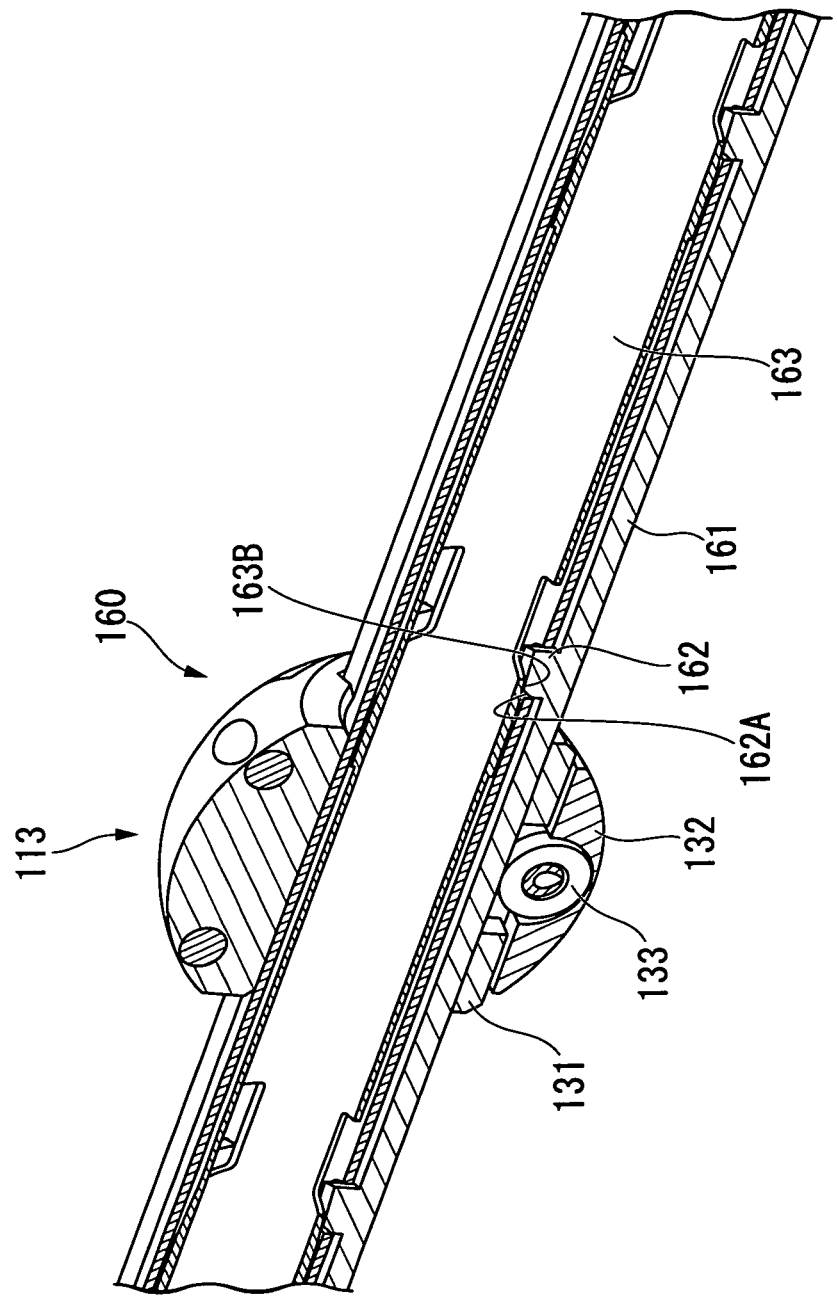
FIG. 23 is a cross-sectional view when the pivot locking mechanism is operated.
Figure 24:
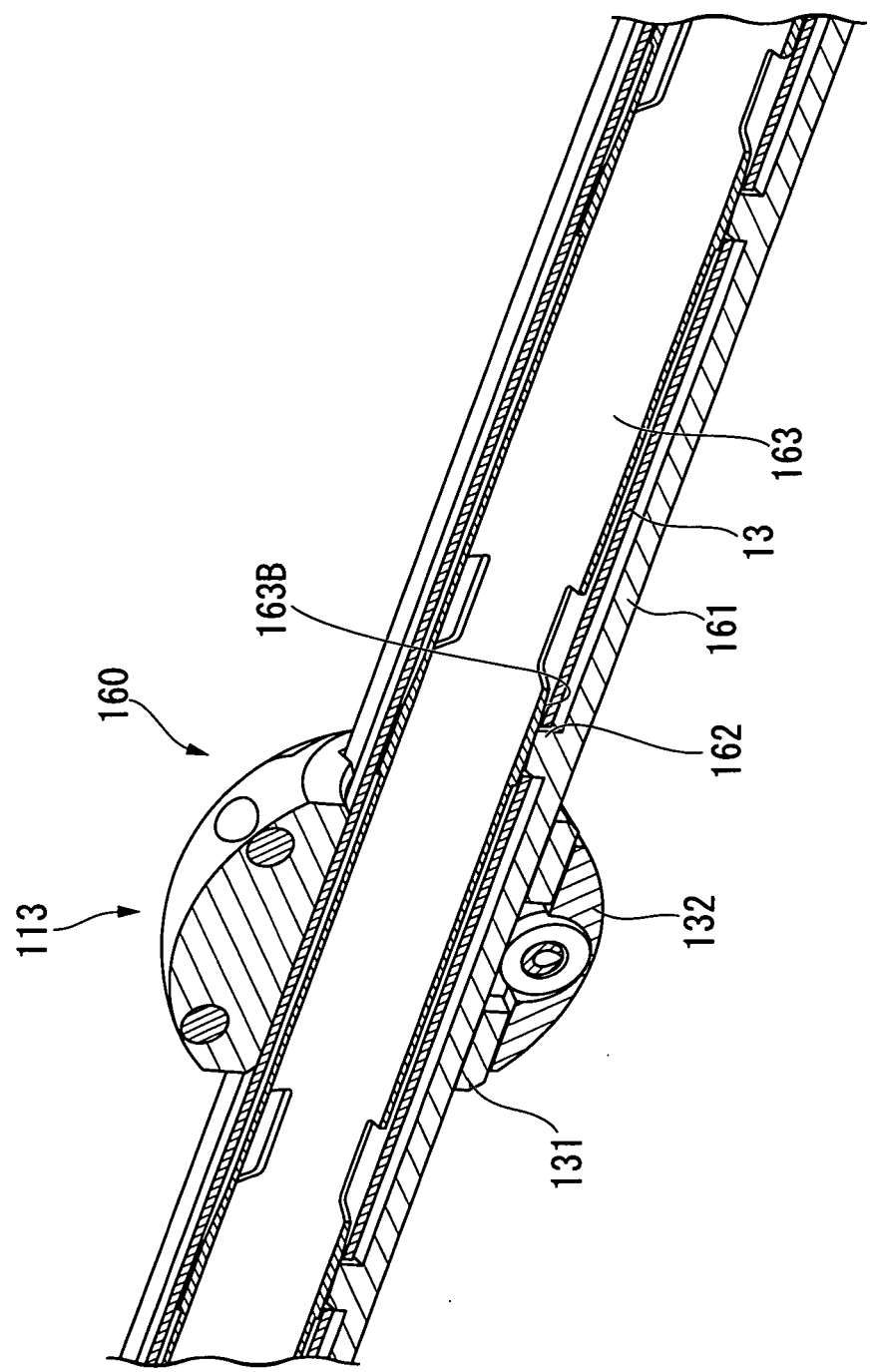
FIG. 24 is a cross-sectional view when the pivot locking mechanism is operated.

Moreover, if the locking lever 81 is pulled up, the bearings 133 and the movable members 132 are pushed up, and as shown in FIG. 23, the rail members 161 and the base members 131 come into contact with each other. After that, all of the respective regions 121, 122 and the 123 are pushed up so as to separate from the outer peripheral surface of the outer pipe 13 along with the retreat of the locking pipe 163. If the locking lever 81 is completely pulled up, the legs 162 of the rail members 161 ride on the inclination surface 163B of the locking pipe 163, and projection ends of the legs 162 and the outer peripheral surface of the locking pipe 163 come into contact with each other. Therefore, as shown in FIG. 24, each region of the spherical portion 113 separates from the outer peripheral surface of the outermost pipe 13. In this state, the contact pressure with the first tubular portion 111 and the second tubular portion 112 is increased in the overall outer peripheral surface of the spherical portion 113, and as a result, the pivot operation of the insertion portion 10 is completely locked. Moreover, since the bearings 133 also no longer function substantially, the advance or retreat operation of the insertion portion 10 is also locked. Since the position of the locking pipe 163 is maintained by frictional forces generated between the locking pipe and the legs 162, there is no case in which the insertion portion advances naturally if the locking lever 81 is not operated. Accordingly, even if the user removes use's hand from the locking lever 81, the operating state of the pivot locking mechanism 160 is maintained.

As described above, the locking lever 81 is connected to both the bending locking mechanism 150 and the pivot locking mechanism 160. If the locking lever 81 is completely distal endped to the proximal end side, only the bending operation is locked and the pivot operation and advance or retreat operation of the insertion portion 10 are enabled, and if the locking lever 81 is completely pulled up, the pivot operation and the advance or retreat operation are locked, and only the bending operation is enabled. In addition, when the locking lever 81 is midway between both states, the weight of the pivot operation varies. Additionally, since all the operations can be performed, three types of states can be produced by the operation of the locking lever 81.

Accordingly, the locked state of the bending operation and the locked state of the pivot operation can be suitably switching simply by operating the locking lever 81. As a result, the user can reliably separate these operations without skill or the like, and can operate the treatment portion 30 of the distal end of the insertion portion 10 as intended.

Additionally, since the locked state of the bending operation and the locked state of the pivot operation are suitably maintained even if the user removes user's hand from the locking lever, the user does not need to continue operating the locking lever and operation is kept from becoming complicated.

Moreover, since the rail members 161 are attached to the insertion portion 10, a radial cross-section of the whole insertion portion 10 is formed into a non-circular shape having a projection in which a portion of a circular shape protrudes. For this reason, the insertion portion 10 and the spherical portion 113 are not rotatable relative to each other, and the insertion portion 10 can be prevented from rotating around the axis unintentionally while repeating the bending operation in a procedure. Moreover, if a force with a magnitude equal to or greater than a predetermined value is applied, the spherical portion 113 and the insertion portion 10 can be integrally rotated relative to the first tubular portion 111 and the second tubular portion 112. Therefore, an operation can be made such that the insertion portion 10 is rotated in a state where a tissue or the like is gripped by the treatment portion 30.

Operation in Use

Figure 25:
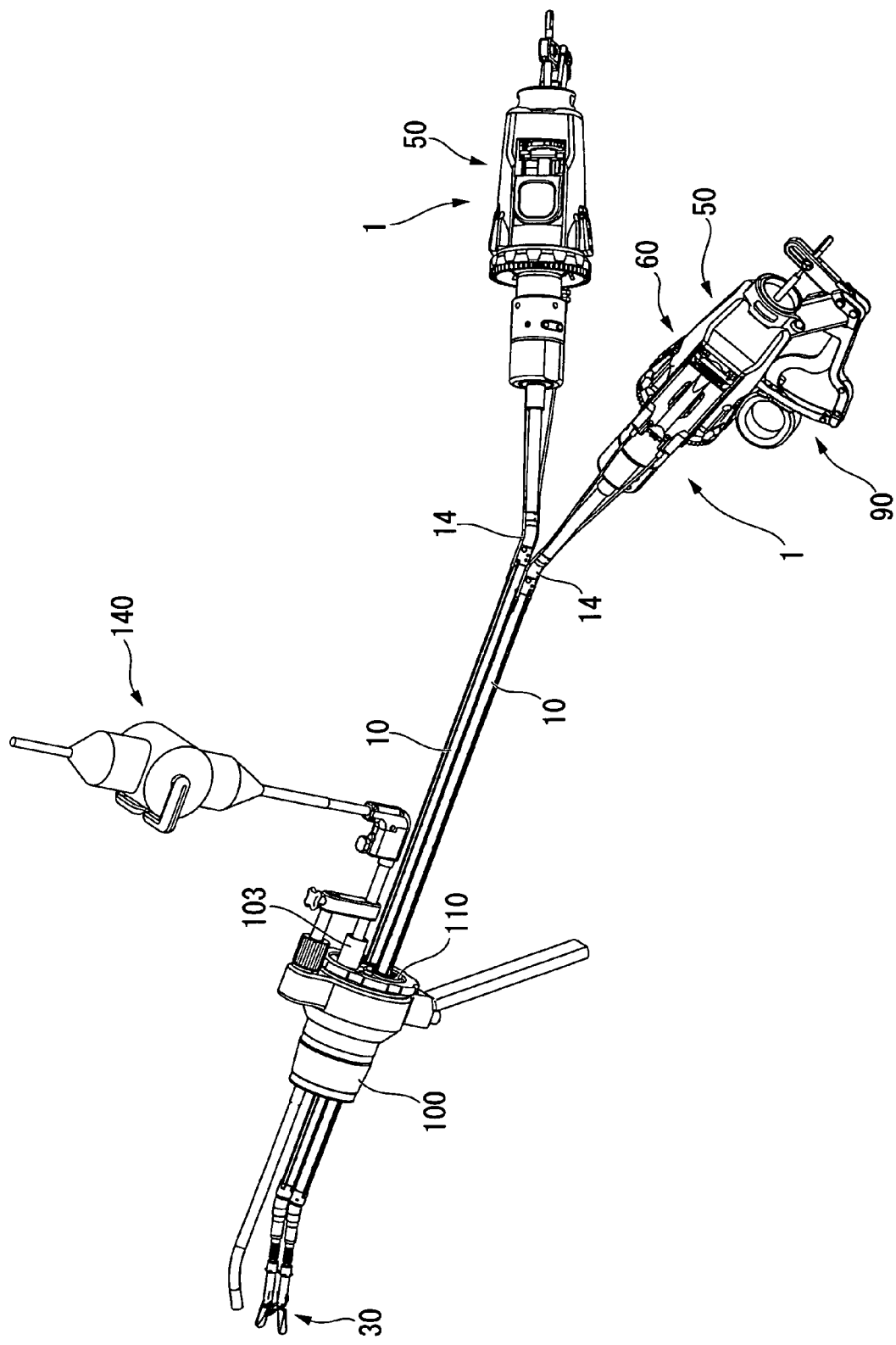
FIG. 25 is a view showing an example of a state where the multi-degree-of-freedom forceps is used.

FIG. 25 is a view showing an example of a state where the multi-DOF forceps 1 is used. The user mounts the pivot portion 110 on the access port 100 installed in the patient, and inserts the insertion portion 10 of the multi-DOF forceps 1 through the pivot portion. Moreover, an endoscope 140 as observation means is inserted into the port 103 for an endoscope. FIG. 25 shows a state where two multi-DOF forceps 1 are inserted into one access port 100. Although the multi-DOF forceps 1 are inserted through the pivot portions 110 mounted on adjacent ports for forceps, respectively, respective operating portions 50 thereof can be arranged apart from each other because the insertion portions 10 have the curved portions 14. Therefore, the respective operating portions 50 can be easily operated. The user grips the operating portion 50 after the second operating portion 90 of the operating portions 50 is rotated relative to the first operating portion 60 if required and is brought into a desired positional relationship. A predetermined procedure is performed by appropriately combining the operation of the first operating portion 60 and the second operating portion 90 and the pivot operation and advance-retreat operation of the insertion portion 10 while observing the treatment portion 30 and its periphery of each multi-DOF forceps 1, with the endoscope 140. When the opening and closing direction of the treatment portion 30 is adjusted, the dial 75 provided on the distal end side of the handle body 71 is rotated. As shown in FIG. 16, the dial 75 is connected to the gear 77 arranged on the proximal end side of the swivel joint portion via a flexible shaft 76 having flexibility. Since the gear 77 is connected to a rotation operating pipe (not shown) connected to the treatment portion 30, the dial 75 can be rotated so as to rotate the treatment portion 30 to adjust the opening and closing direction of a pair of forceps pieces. The locking lever 81 is appropriately operated when the bending operation, the pivot operation, or the like is locked or the locked state is switched.

By the above operation, the user can operate the position of the distal end portion of the insertion portion 10 and the treatment portion 30 in each multi-DOF forceps 1 so as to reliably reflect a user's intention, and suitably perform various procedures on a patient.

Modified Example of Bending Locking Mechanism

A modified Example of the bending locking mechanism will be described. In this modified Example, the locking of the bending operation and the locking of the pivot operation are switched by making a locking button exposed to the outer surface of the handle body slide.

Figure 26:
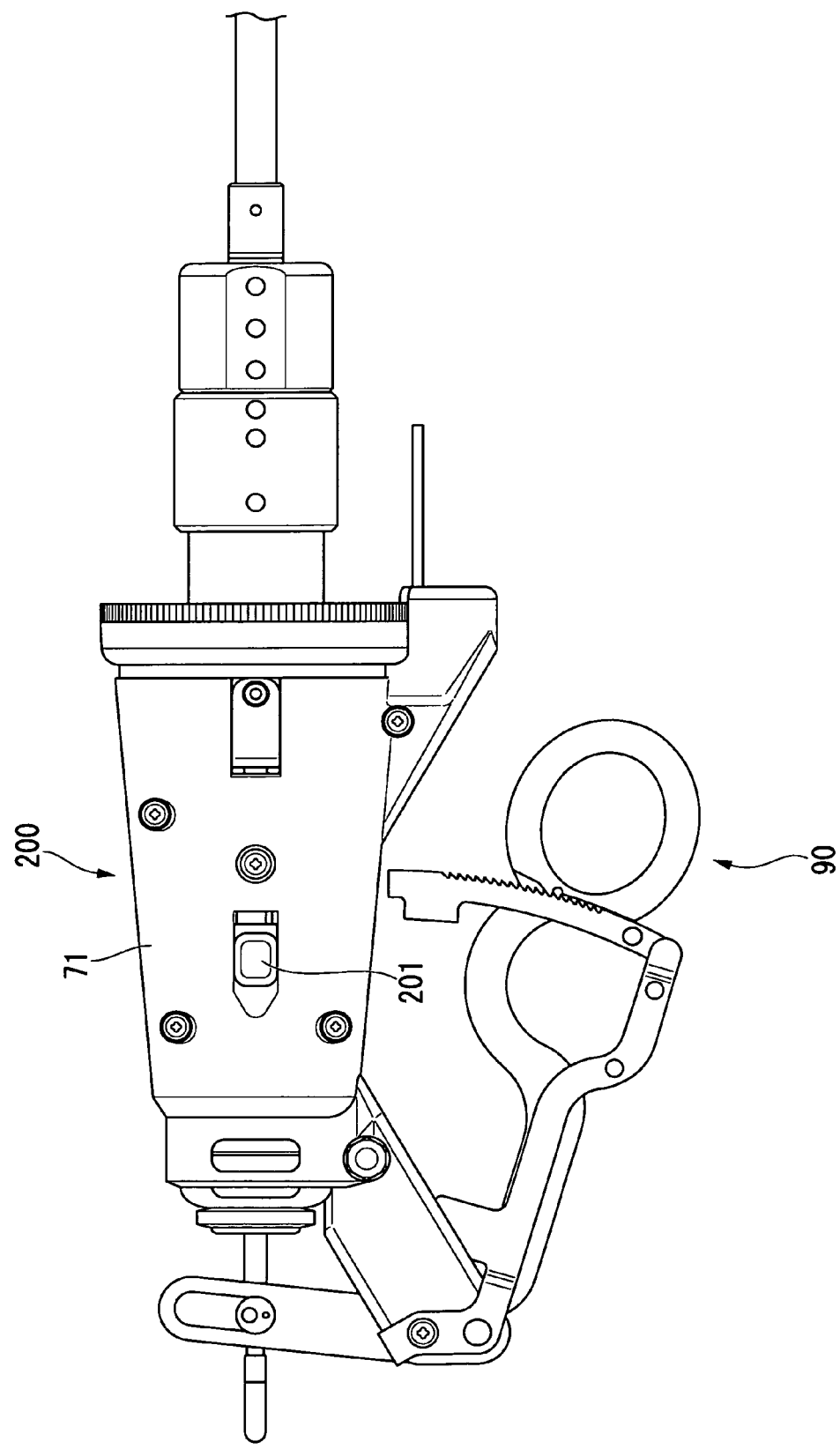
FIG. 26 is a view showing an operating portion in a modified Example of the multi-degree-of-freedom forceps.

FIG. 26 is an external view of an operating portion 200 of this modified Example. In the first operating portion 210, a pair of locking buttons (switching operating portions) 201 are provided in an exposed manner on the outer surface of the handle body 71 instead of the locking lever, and are capable of sliding parallel to the axis direction of the handle body 71.

Figure 27:
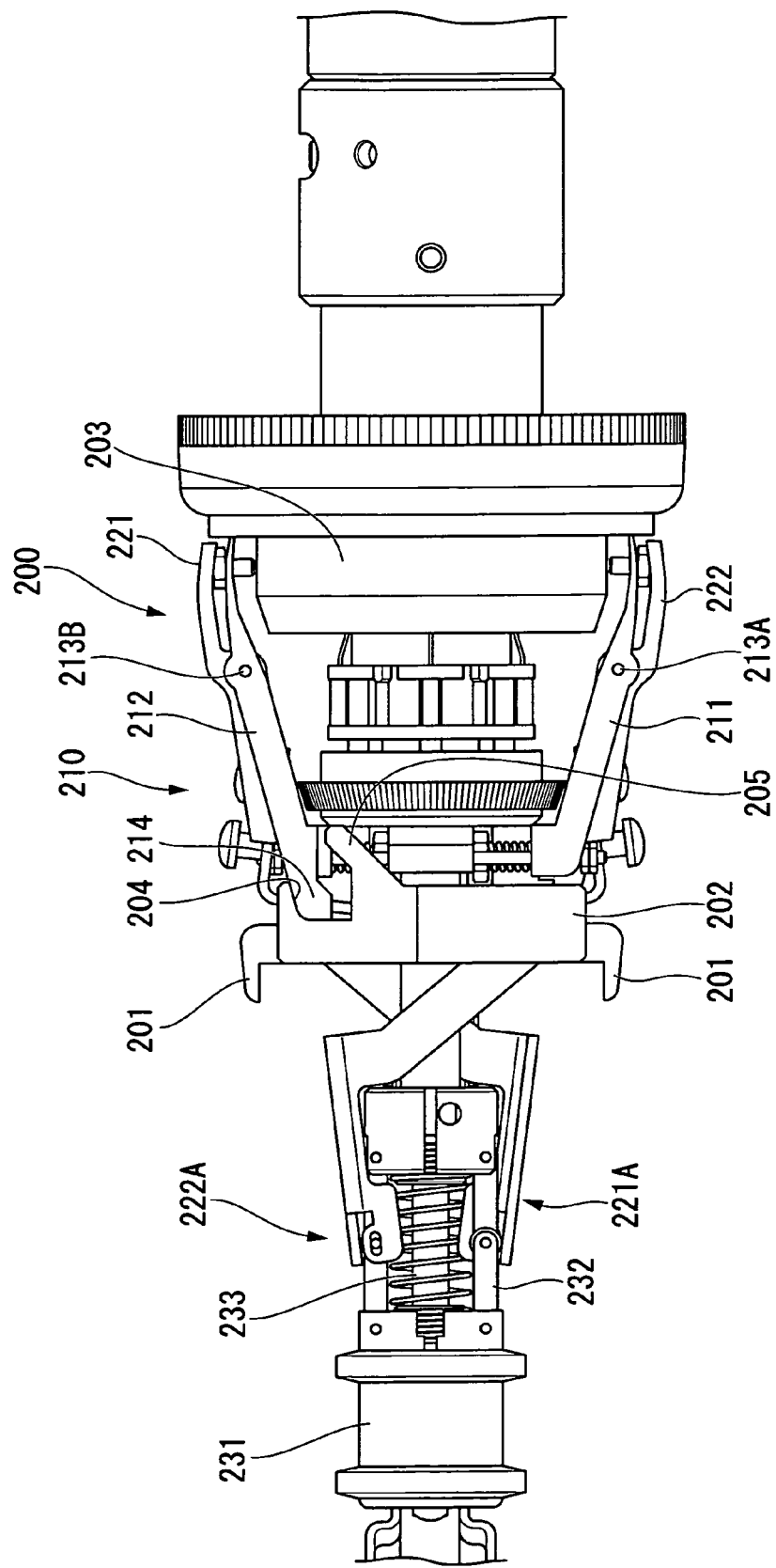
FIG. 27 is a view showing the operating portion excluding the handle body.
Figure 28:
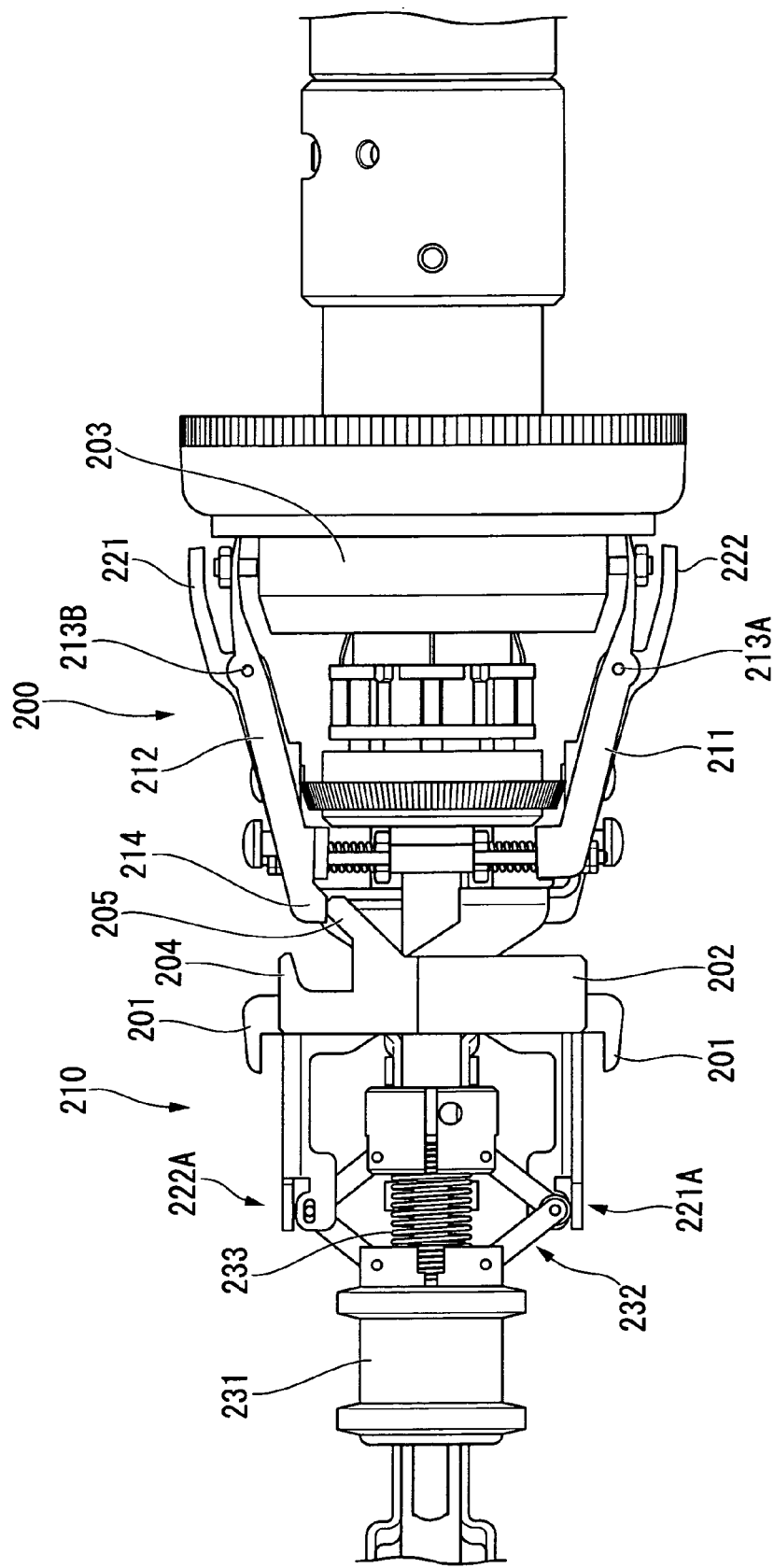
FIG. 28 is a view showing the operating portion excluding the handle body.
Figure 29:
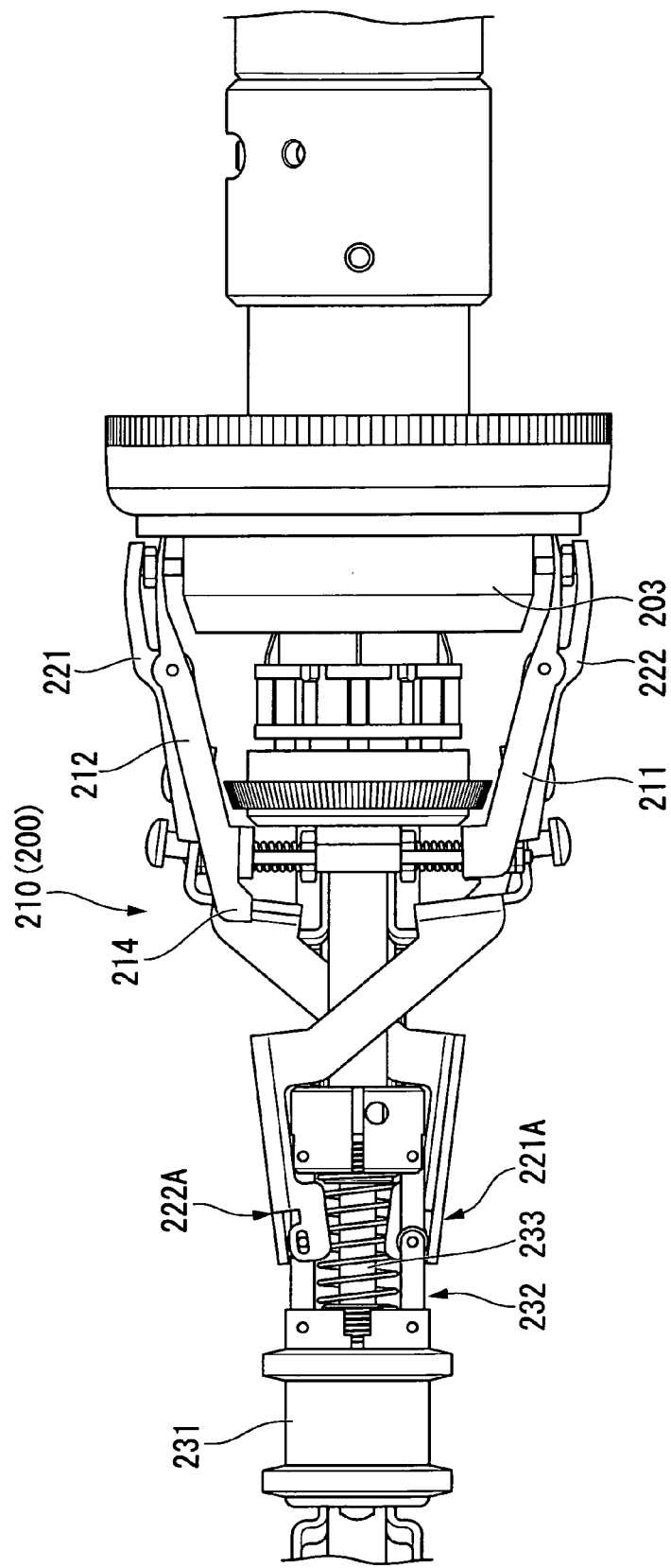
FIG. 29 is a view showing the operating portion excluding the handle body and a slider.
Figure 30:
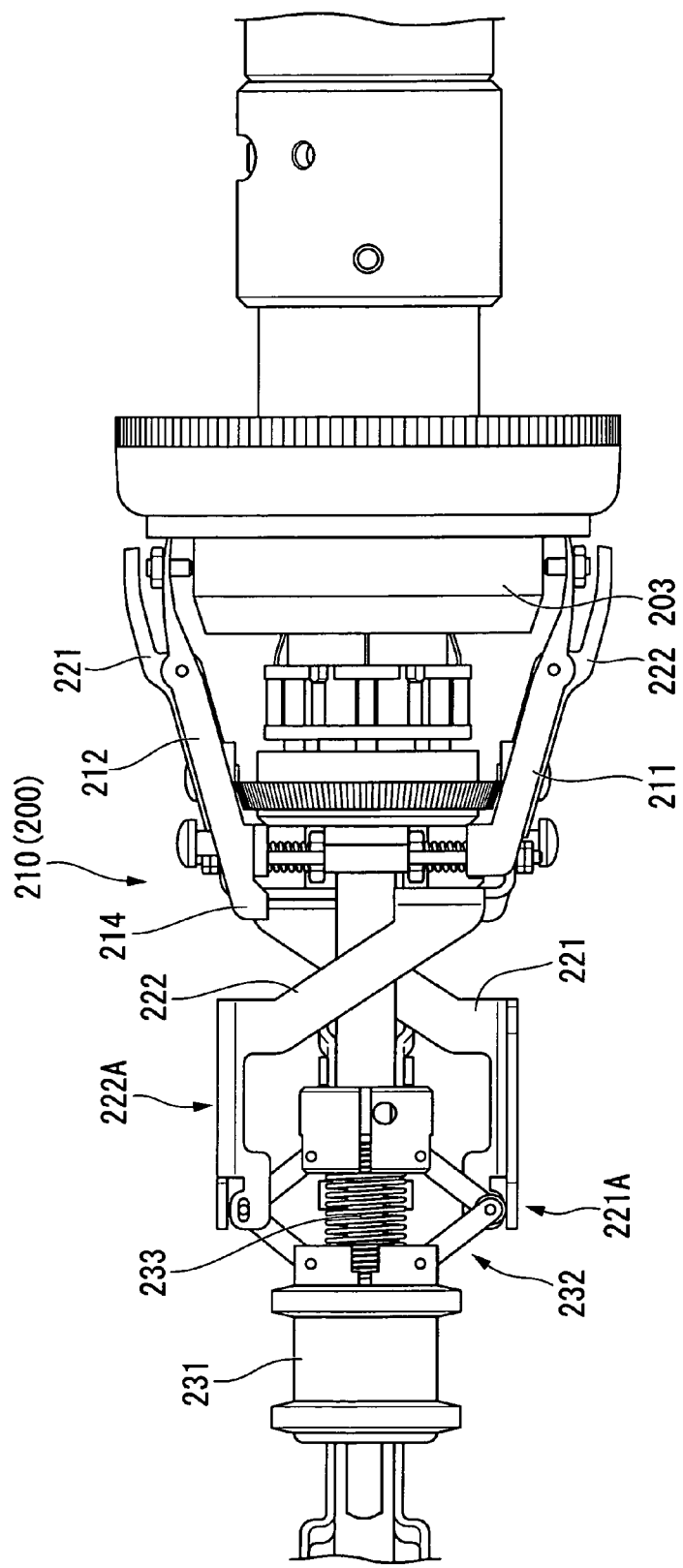
FIG. 30 is a view showing the operating portion excluding the handle body and the slider.

FIGS. 27 and 28 are views of a first operating portion 210 excluding the handle body 71. FIGS. 29 and 30 are views showing the first operating portion 210 further excluding a slider 202 formed with the locking buttons 201.

A pair of locking members that come into contact with a swivel joint portion 203 and lock a bending operation are arranged so as to face each other across the swivel joint portion 203, substantially similar to the first embodiment. One first locking member 211 is connected to a first interlocking member 221 arranged on another second locking member 212 side. Similarly, the second locking member 212 is connected to a second interlocking member 222 arranged on the first locking member 211 side. The first locking member 211 and the second interlocking member 222 are rotatably supported by a pivot shaft 213A, and the second locking member 212 and the first interlocking member 221 are rotatably supported by a pivot shaft 213B. Therefore, the first locking member 211 and the first interlocking member 221 rotate in the same direction in an interlocking manner, and the second locking member 212 and the second interlocking member 222 rotate in the same direction in an interlocking manner.

As shown in FIGS. 29 and 30, the first interlocking member 221 and the second interlocking member 222 intersect each other closer to the proximal end side than the pair of locking members 211 and 212, and extend to the first locking member 211 side and the second locking member 212 side, respectively. Proximal end portions 221A and 222A of the respective interlocking members 221 and 222 are connected to a link portion 232 that advances and retreats an advancing-retreating member 231 in the axis direction of the operating portion 200. A flexible shaft 233 connected to the locking pipe 163 is connected to the advancing-retreating member 231. If the advancing-retreating member 231 advances and retreats, the locking pipe 163 is advanced and retreated via the flexible shaft 233. The structure of the pivot locking mechanism is the same as that of the first embodiment.

Proximal end portions of the pair of locking members 211 and 222 are provided with projections 214 that come into contact with the slider 202 to rotate the locking members. As shown in FIGS. 27 and 28, the slider 202 is provided with a first contact portion 204 that comes into contact with the outside of a projection 214 and a second contact portion 205 that comes into contact with the inside of the projection 214. Only the projection 214 of the second locking member 212 is seen in FIGS. 27 and 28. Although not shown, the same projection 214 is also provided on the first locking member 211 on the back side (the side behind a sheet plane in FIGS. 27 and 28). The slider 202 is also formed with corresponding first and second contact portions 204 and 205.

The operation of the operating portion 200 of this modified Example will be described. FIGS. 27 and 29 show a state where the locking buttons 201 have been operated and the slider 202 has advanced. If the slider 202 advances, the first contact portions 204 and the outer side of the projections 214 of the pair of locking members 211 and 212 come into contact, and the pair of locking members rotate so that the proximal end portions thereof approach each other. As a result, distal end portions of the locking members move so as to separate from each other and are separated from the swivel joint portion 203, and are brought into a state where the bending operation is possible. At this time, the first interlocking member 221 and the second interlocking member 222 also rotate in interlocking with the pair of locking members 211 and 212. As a result, the proximal end portion 221A of the first interlocking member 221 and the proximal end portion 222A of the second interlocking member 222 move so as to approach each other, and make the link portion 232 linear. As a result, the advancing-retreating member 231 retreats, the locking pipe 163 retreats, and the pivot locking mechanism 160 operates. The locked state of the pivot operation is maintained by frictional forces generated between the projections 214 and the first contact portions 204.

FIGS. 28 and 30 show the state where the slider 202 has retreated. If the slider 202 retreats, the second contact portions 205 and the inside of the projections 214 of the pair of locking members 211 and 212 come into contact with each other, and the pair of locking members rotate so that the proximal end portions thereof separate from each other. As a result, the distal end portions of the locking members move so as to approach each other and come into contact with the swivel joint portion 203 to thereby lock the bending operation by pressing. At this time, the first and second interlocking members 221 and 222 are also rotated in interlocking with the pair of locking members 211 and 212, and the proximal end portions 221A and 222A of the first and second interlocking members move so as to separate from each other, and bend the link portion 232. As a result, the advancing-retreating member 231 advances and is brought into a state where the pivot operation is possible. The locked state of the bending operation is maintained by frictional forces generated between the projections 214 and the second contact portions 205.

Even in the above configuration, the user can suitably switch the locked state of the bending operation and the locked state of the pivot operation by operating the locking buttons 201 to advance and retreat the slider 202.

Second Embodiment

A second embodiment of the present invention will be described with reference to FIGS. 31 to 36. A multi-DOF forceps 301 of the present embodiment is different from the multi-DOF forceps 1 of the first embodiment in several respects including the first operating portion. In the following description, the same components as those already described will be designated by the same reference numerals, and duplicate description will be omitted.

Figure 31:
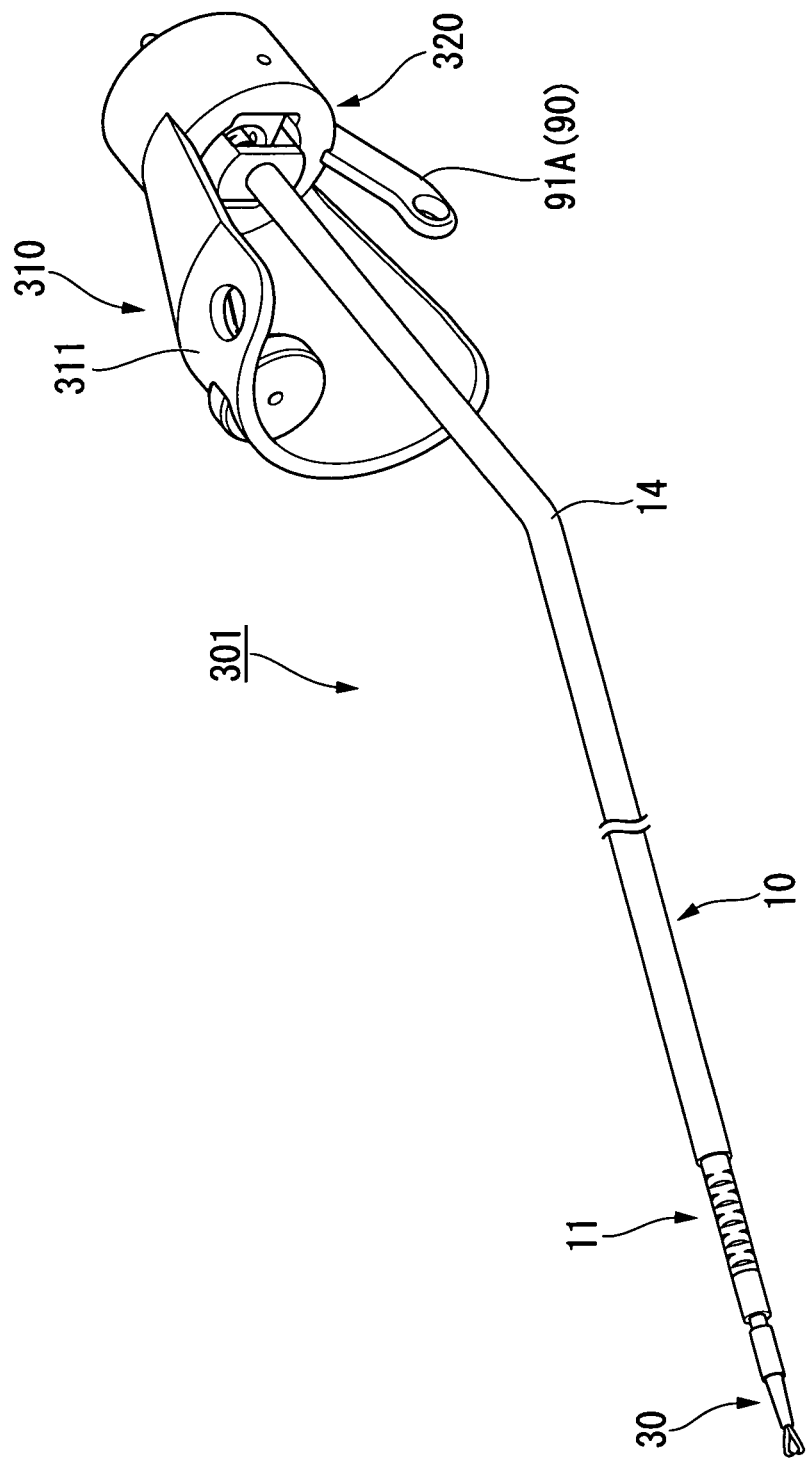
FIG. 31 is an overall view showing a multi-degree-of-freedom forceps of a second embodiment of the present invention.

FIG. 31 is an overall view of the multi-DOF forceps 301. A first operating portion 310 includes a joint portion 320 instead of the swivel joint portion 61, and a handle body 311 is different in shape from the handle body 71 of the first embodiment. Additionally, in the present embodiment, the handle body 311 is provided closer to the insertion portion 10 side than the operation center of the second bending portion 12.

Figure 32:
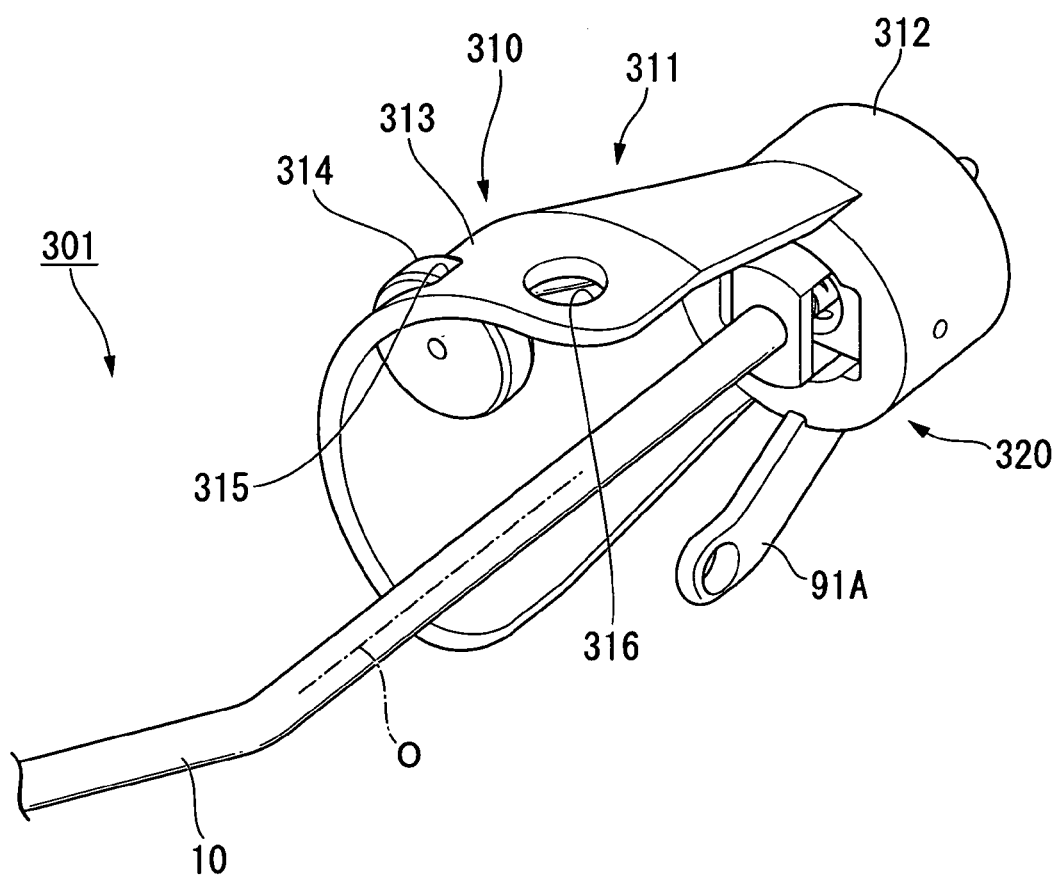
FIG. 32 is an enlarged view of a first operating portion of the multi-degree-of-freedom forceps.

FIG. 32 is an enlarged view of the first operating portion 310. The handle body 311 includes a cylindrical proximal end portion 312 to which the joint portion 320 is attached, and a grip portion 313 that extends to the treatment portion 30 side from the proximal end portion 312. The grip portion 313 has a shape in which a portion of the peripheral wall of a substantially hollow truncated conical shape is removed, and is provided with two holes of a knob hole 315 for exposing a rotating knob 314 used for the rotational operation of the insertion portion 10 of the treatment portion 30 and a finger hooking hole 316. As shown in FIG. 32, the rotating knob 314 is provided apart from the axis O of the insertion portion 10. Additionally, as shown in FIG. 31, the rotating knob 314 is connected to the treatment portion 30 via a shaft (flexible shaft 317 to be described below) having flexibility.

Although an opening and closing lever 91A is slightly different in shape from the opening and closing lever 91 of the first embodiment, the operating methods or functions thereof are the same as those of the opening and closing lever 91.

Figure 33:
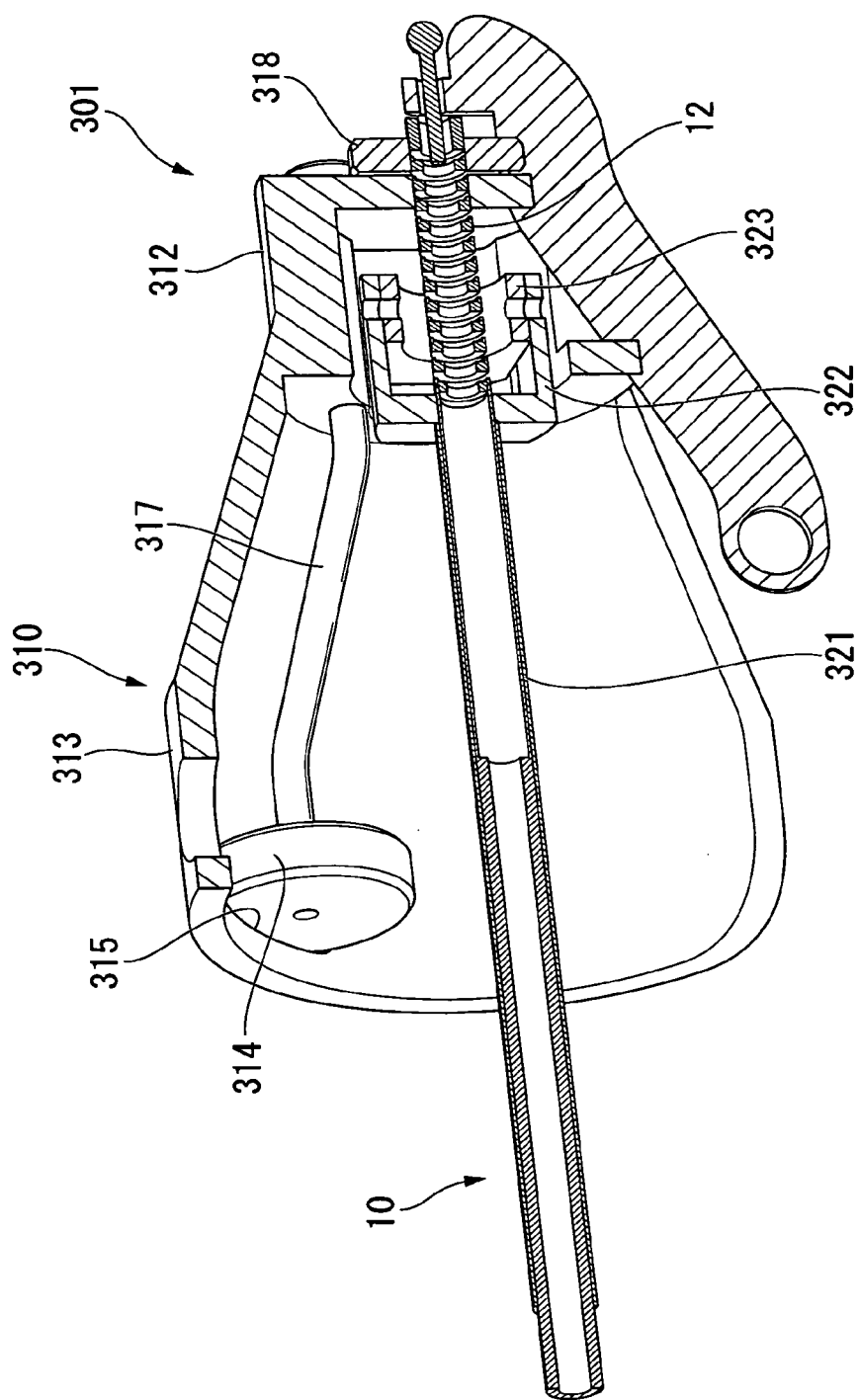
FIG. 33 is a cross-sectional view of the first operating portion.

FIG. 33 is a cross-sectional view of the first operating portion 310. A mechanism for rotating the treatment portion 30 includes substantially the same structure as the first embodiment. The flexible shaft (shaft) 317 connected to the rotating knob 314 provided instead of the dial is connected to a gear 318 that rotates the rotation operating pipe at the rear portion of the handle body 311. The rotating knob 314 is partially exposed through the knob hole 315, and the user can rotate the rotating knob 314 to adjust the opening and closing direction of the treatment portion 30 in a state where the user has gripped the grip portion 313.

Figure 34:
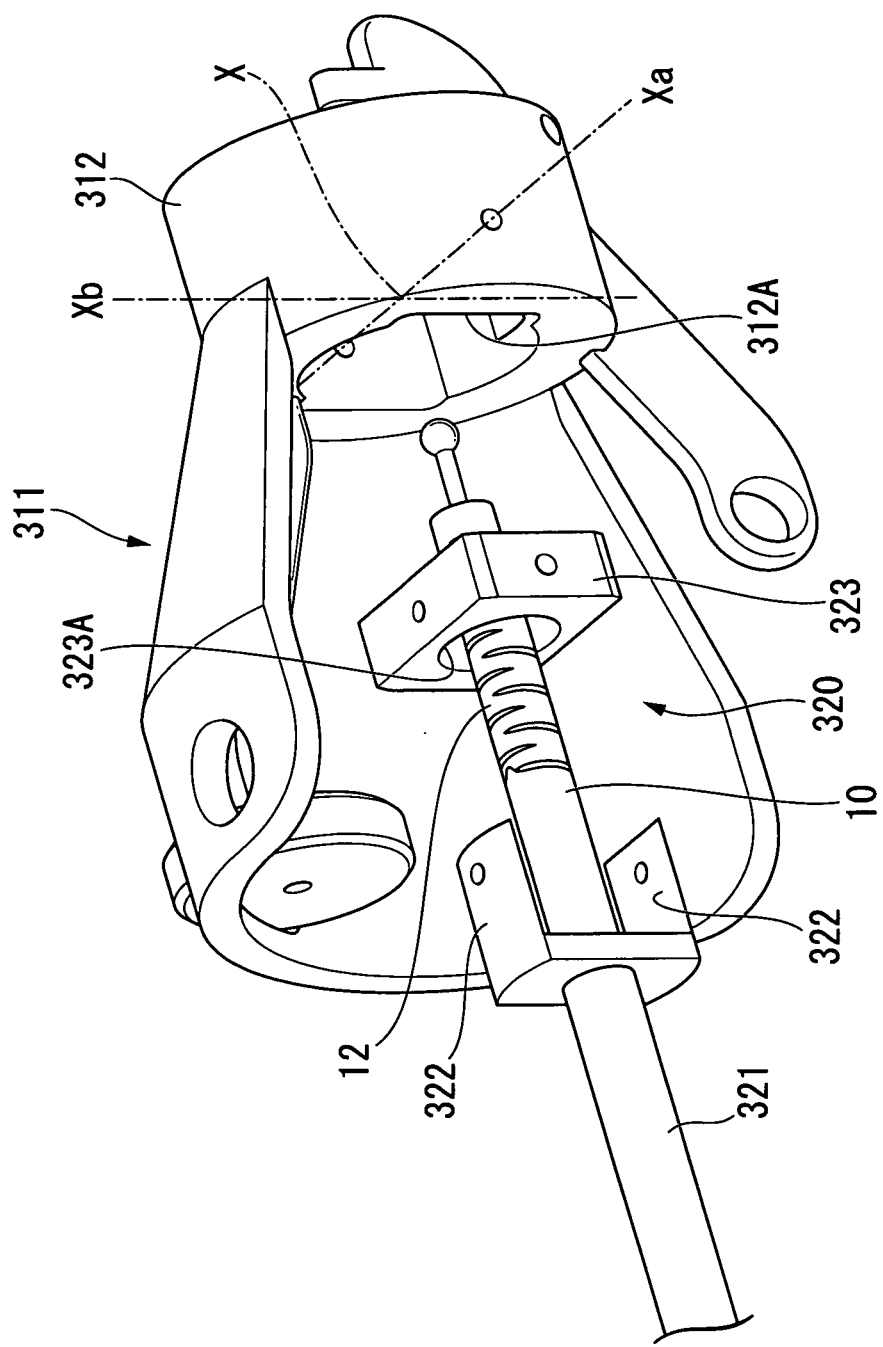
FIG. 34 is an exploded view showing a joint portion of the first operating portion.

FIG. 34 is an exploded view of the joint portion 320. The proximal end side of the insertion portion 10 is inserted into an outer tube 321, and a proximal end portion of the outer tube 321 is provided with a pair of facing fixed walls 322. The fixed walls 322 are fitted into a hole 312A formed in the proximal end portion 312 of the handle body 311 and are fixed to the handle body 311. The second bending portion 12 is inserted through a through hole 323A of a rotary body 323, and the rotary body 323 is arranged so as to substantially coincide with the center of the second bending portion 12 in the longitudinal direction. The basic shape of the rotary body 323 is a substantially rectangular parallelepiped, and as shown in FIG. 34, and the rotary body is arranged within a hole 312A so as to be located between the pair of fixed walls 322 in a state with the long sides thereof being parallel to the fixed walls 322. The rotary body 323 is supported so as to be rotatable relative to the handle body 311 on two axes of a first axis Xa parallel to the long sides and a second axis Xb parallel to short sides and orthogonal to the first axis Xa, by four cantilevered shafts that are not shown. A pair of cantilevered shafts that rotatably support the rotary body 323 on the second axis Xb are attached to the rotary body 323 through the pair of fixed walls 322.

From the above structure, the joint portion 320 has a so-called biaxial gimbal structure, and the handle body 311 can be swung around the first axis Xa and the second axis Xb with an intersection point between the first axis Xa and the second axis Xb as the operation center X. However, since the outer tube 321 is assembled so as not to be rotatable relative to the handle body 311, relative rotation of the handle body 311 and the joint portion 320 around the axis of the insertion portion 10 can be regulated.

Figure 35:
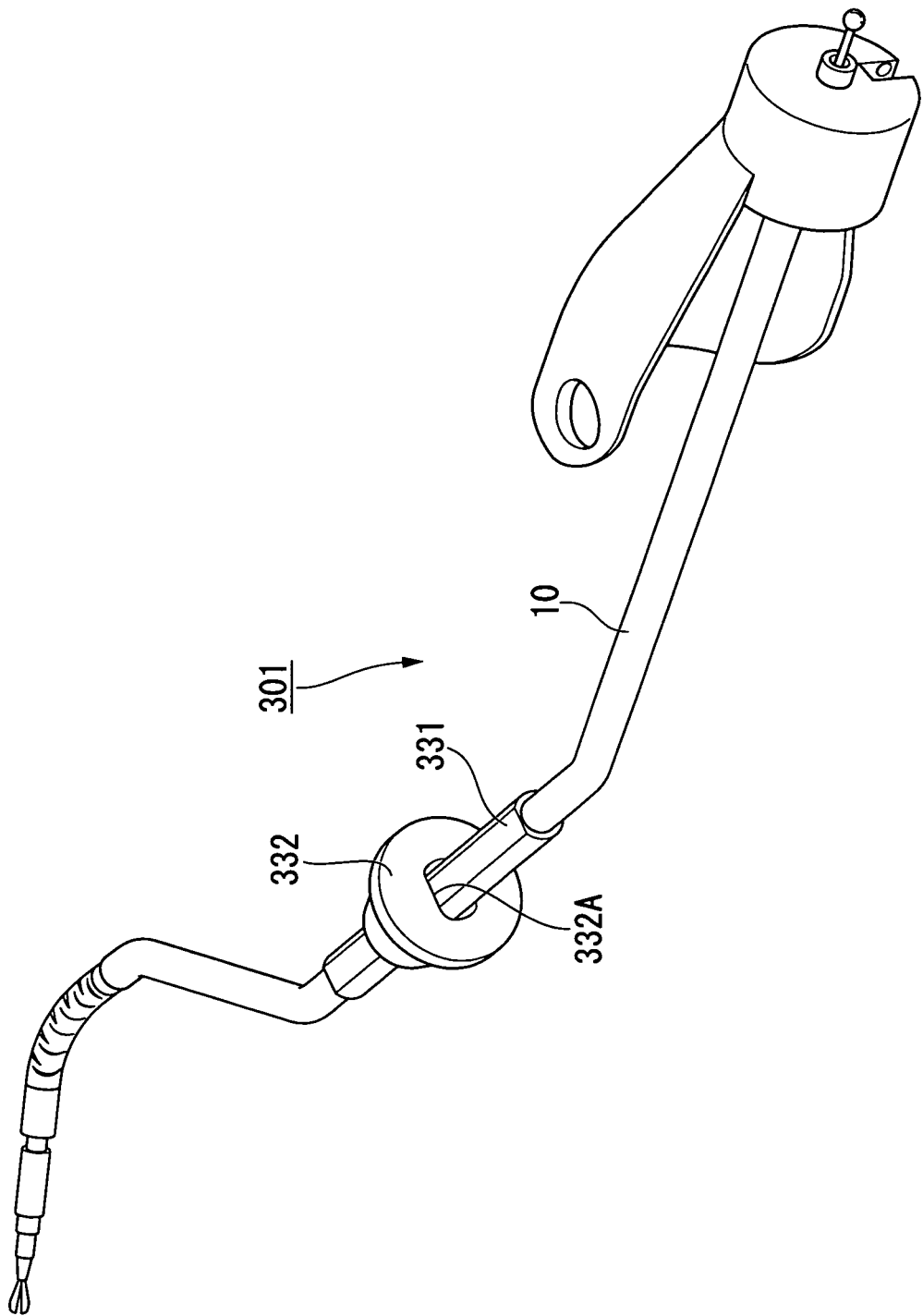
FIG. 35 is a view showing an insertion portion when the multi-degree-of-freedom forceps is used.

Although the multi-DOF forceps 301 does not include the pivot locking mechanism or the bending locking mechanism and the mechanism that switches locked states, as shown in FIG. 35, a rotation-regulating member 331 is attached to an intermediate part of the insertion portion 10 located within the access port in use, and the cross-sectional shape of the outer peripheral surface thereof is a non-circular oval shape. Since an insertion hole 332A of the access port 332 has the same shape as the appearance of the rotation-regulating member 331, the access port 332 and the insertion portion 10 basically do not rotate relatively. Therefore, the insertion portion 10 is kept from rotating around the axis relative to the access port 332 while repeating the bending operation. On the other hand, since the cross-section of the insertion portion 10 is circular, if a constant force is made to act on the insertion portion 10, it is also possible to rotate the insertion portion 10 relative to the rotation-regulating member 331.

The cross-sectional shape of the outer peripheral surface of the rotation-regulating member 331 may be other shapes, such as a polygonal shape when the cross-sectional shape is noncircular. Additionally, the shape of the insertion hole of the spherical portion of the pivot portion 110 in the first embodiment instead of the access port 332 may be made to correspond to the rotation-regulating member, and the insertion portion 10 may be inserted through the pivot portion 110.

Figure 36:
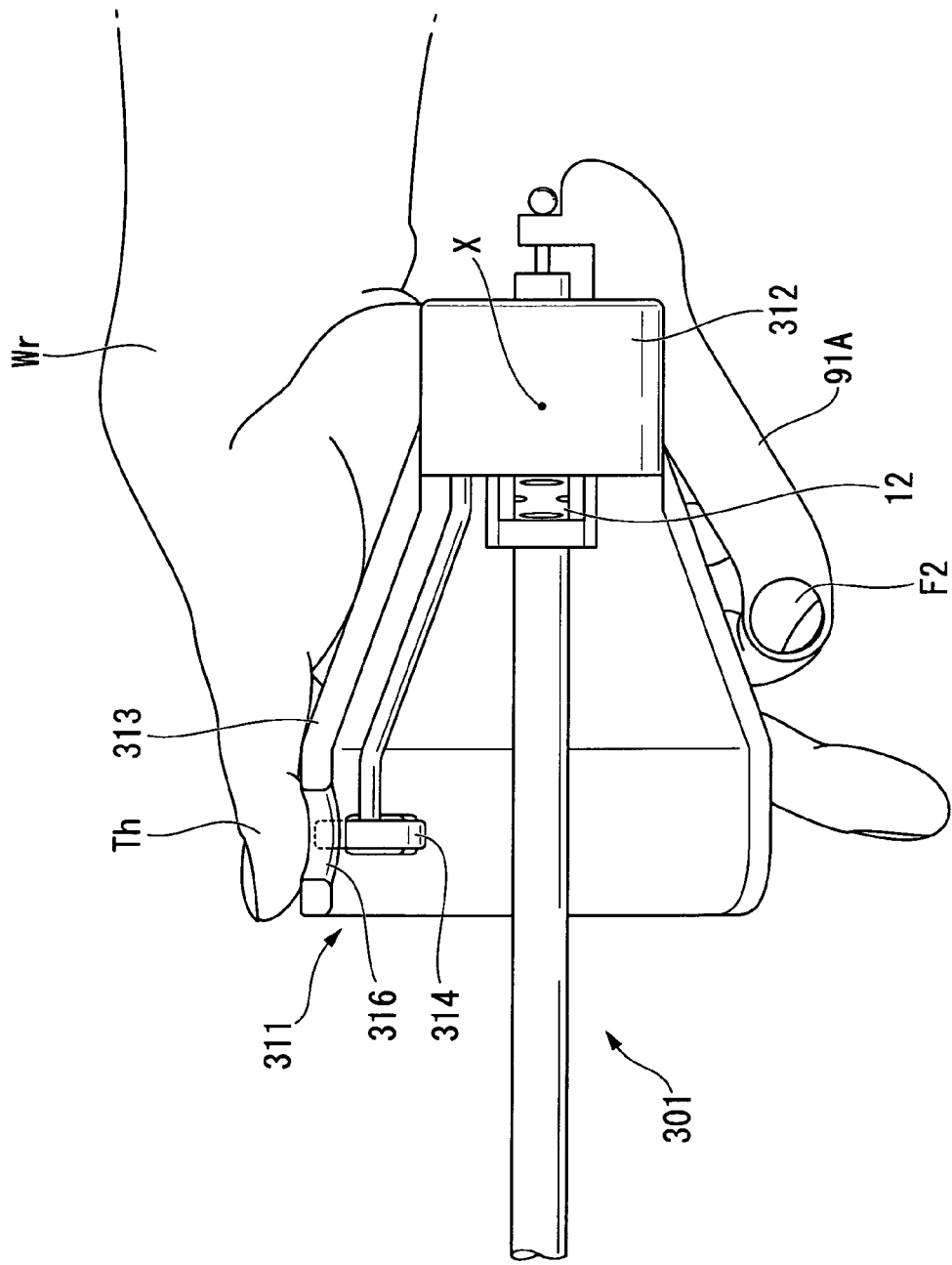
FIG. 36 is a view showing a state where a user grips the first operating portion of the multi-degree-of-freedom forceps.

When the multi-DOF forceps 301 of the present embodiment is used, as shown in FIG. 36, the user applies user's wrist Wr to the proximal end portion 312 of the handle body 311 and grips the grip portion 313 so as to wrap around the grip portion. Then, an operation is made in a state where a thumb Th is applied to the finger hooking hole 316 and a middle finger F2 is hooked to the opening and closing lever 91A. During the bending operation for bending the first bending portion 11, a hand that has gripped the grip portion 313 is moved in a desired direction to perform the swinging operation of the handle body 311, and when the pivot operation is performed, a distal end is fixed from the wrist Wr and the whole arm is moved.

According to the multi-DOF forceps 301 of the present embodiment, the second bending portion 12 is located at the proximal end portion 312 of the handle body 311, and the grip portion 313 is located closer to the distal end side than the second bending portion 12. Therefore, the handle body 311 is gripped in a state where the operation center X of the handle body in the bending operation and the position of the wrist Wr are made to substantially coincide with each other in the direction of the axis of the first operating portion 310. The wrist is a part where a joint that connects a hand and an arm is located, and hardly moves even if the hand is moved in any way. Accordingly, even if the hand grips the handle body 311 and is moved, a moment that makes the insertion portion 10 produce the pivot operation is hardly generated. Therefore, by performing operation as described above, a procedure can be performed while the bending operation from the pivot operation is suitably separated without advanced skill.

Although the respective embodiments of the present invention have been described above, the present invention is not limited to the above embodiments, and various modifications can be added to the respective constituent elements, omissions can be made from the constituent elements, and the constituent elements of the respective embodiments can be combined, without departing from the spirit of the present invention.

For example, although the multi-DOF forceps including the bending locking mechanism and the pivot locking mechanism has been described in the above-described first embodiment, a configuration including only one of the mechanisms instead of this may be used. In this case, although the ease of operation deteriorates slightly, the bending operation and the pivot operation can be separated and operated by locking one operation to carefully perform the other operation.

Additionally, the part that operates the bending locking mechanism and the part that operates the pivot locking mechanism may not be the same but may be separably provided, respectively. Even in this case, although operability decreases slightly as compared with the respective embodiments, the bending operation and the pivot operation can be separably operated.

Moreover, the rotating knob that rotates the treatment portion may be directly attached to the insertion portion without interposing the flexible shaft. In this case, the grip portion can be arranged at an operable position while being gripped by exposing a portion of the rotation operating pipe at a position closer to the distal end side than the proximal end of the insertion portion and connecting the rotating knob to the exposed part.

Moreover, a configuration may be formed where the grip portion may be formed from an elastically deformable material, and the user may apply a force to the grip portion to elastically deform the grip portion so as to bring the grip portion into close contact with the swivel joint portion. If the user elastically deforms the grip portion in this way, it is possible to increase the frictional force between the grip portion and the swivel joint and to temporarily apply locking to the bending operation.

According to the above multi-DOF forceps, since the grip portion is arranged around the operation center, the user can easily and separably operate the bending operation of the first bending portion and the pivot operation of the insertion portion, without requiring advanced skill.

All the constituent elements described in the above respective embodiments and modified Examples can be carried out by appropriate combinations or omissions within the scope of the technical idea of the present invention. Moreover, although the preferred examples of the present invention have been described above, the present invention is not limited to these examples. Additions, omissions, substitutions, and other modifications can be made without departing from the spirit of the present invention. The present invention is not to be considered as being limited by the foregoing description, and is limited only by the scope of the appended claims.

The invention claimed is:

1. A multi-degree-of-freedom forceps system comprising:
   a multi-degree-of-freedom forceps comprising:
      an insertion portion which is longitudinal, extends along a longitudinal axis, and has a joint portion at a proximal end portion, an operating portion which has a handle body, the handle body being coupled to the joint portion so as to be rotatable in a direction intersecting the longitudinal axis of the insertion portion, and the handle body being provided so as to be capable of swinging and operating relative to the insertion portion, a bending portion which is provided at a distal end portion of the insertion portion so as to be bendable relative to the longitudinal axis of the insertion portion according to a swinging operation of the handle body relative to the insertion portion, and a bending locking mechanism which enables fixation of the rotation of the insertion portion in the direction intersecting the longitudinal axis of the insertion portion relative to the handle body, and release of the fixation; and an access port that is mountable on a body wall, the access port comprising:

a port portion into which the insertion portion is inserted, and a pivot portion that supports the insertion portion so that the insertion portion is movable along the longitudinal axis of the insertion portion, and that supports the insertion portion so that only the insertion portion is pivotally operable relative to the access port, wherein:

the pivot portion has a pivot locking mechanism which is capable of locking at least one of a pivot operation of the insertion portion with respect to the access port, and a longitudinal movement of the insertion portion in a direction of the longitudinal axis of the insertion portion, the pivot portion includes:

a first tubular portion that is provided inside the port portion along a longitudinal axis of the pivot portion, a second tubular portion that is connected end-to-end with the first tubular portion in a direction along the longitudinal axis of the pivot portion, and a spherical portion that is disposed between the first tubular portion and the second tubular portion and into which only the insertion portion is inserted, the spherical portion being configured to rotate with respect to the first tubular portion and the second tubular portion so as to be capable of oscillating relative to the port portion, and the operating portion includes a switching operating portion which is connected to the bending locking mechanism and the pivot locking mechanism and which switches the lock or the release of each of the bending locking mechanism and the pivot locking mechanism.

2. The multi-degree-of-freedom forceps system according to claim 1, wherein the switching operating portion further performs switching to a state where the bending locking mechanism and the pivot locking mechanism are both released.

3. The multi-degree-of-freedom forceps system according to claim 1, wherein:

a distal end portion of a locking member of the bending locking mechanism is provided so as to be movable from a position apart from the joint portion to a position where the distal end portion of the locking member is locked to the joint portion, and as the distal end portion of the locking member is locked to the joint portion, the locking member fixes the handle body to the insertion portion in the direction intersecting the longitudinal axis of the insertion portion.

4. The multi-degree-of-freedom forceps system according to claim 1, wherein:

a movable member of the pivot locking mechanism is provided so as to be movable from a position apart from the pivot portion to a position where the pivot portion is pressed, and as the movable member presses the pivot portion, the pivot locking mechanism locks at least one of the pivot operation and the longitudinal movement of the insertion portion.

5. The multi-degree-of-freedom forceps system according to claim 1, further comprising:

a treatment portion that is attached to the bending portion and is used for tissue treatment, wherein:

the operating portion has a rotating knob that is provided apart from the longitudinal axis of the insertion portion and rotates the treatment portion relative to the insertion portion, and the rotating knob is connected to the treatment portion via a shaft having flexibility.

6. The multi-degree-of-freedom forceps system according to claim 1, wherein:

the operating portion is attached to the joint portion so as to be capable of swinging relative to the insertion portion, the joint portion has a spherical first member, and a spherical second member that is attached so as to be rotatable around a first rotation axis of the first member, and the handle body is attached so as to be rotatable around a second rotation axis of the second member, the second rotation axis being orthogonal to the first rotation axis.

7. The multi-degree-of-freedom forceps system according to claim 6, wherein:

an outer periphery of the first member is formed with a first engaging protrusion, an outer periphery of the second member is formed with a second engaging protrusion, the first member and the second member are arranged so that a first plane including the first engaging protrusion and a second plane including the second engaging protrusion intersect each other, and the bending direction of the bending portion is regulated so that the bending portion bends along the first plane and the second plane.

8. The multi-degree-of-freedom forceps system according to claim 1, wherein the operating portion is attached to the insertion portion via a biaxial gimbal structure.

9. The multi-degree-of-freedom forceps system according to claim 1, wherein the switching state of the switching operating portion is maintained even if a user removes user's hand from the switching operating portion.

10. The multi-degree-of-freedom forceps system according to claim 1, wherein a radial cross-section of the insertion portion is non-circular and is impossible to rotate relative to the access port when the access port is attached to a patient.

11. The multi-degree-of-freedom forceps system according to claim 1, wherein the spherical portion has a through hole, and a part of the spherical portion is arranged in a lumen of the first tubular portion and the second tubular portion so as to be held by the first tubular portion and the second tubular portion.

12. The multi-degree-of-freedom forceps system according to claim 11, wherein:
a radial cross-section of the insertion portion is non-circular and is impossible to rotate relative to the spherical portion, and
if a force equal to or more than a predetermined value is applied, the insertion portion rotates relative to the first tubular portion and the second tubular portion together with the spherical portion.

13. The multi-degree-of-freedom forceps system according to claim 11, wherein:
the pivot locking mechanism is configured to include the spherical portion, and a rail member attached to the insertion portion, and
the spherical portion has a bearing that reduces the advance or retreat resistance of the insertion portion inserted through the through hole.

14. The multi-degree-of-freedom forceps system according to claim 11, wherein the pivot portion has an airtight portion that is provided in the lumen of at least one of the first tubular portion and the second tubular portion and maintains an airtight state of an inner cavity of the access port.

15. The multi-degree-of-freedom forceps system according to claim 11, wherein the pivot portion is detachable relative to the access port.

16. The multi-degree-of-freedom forceps system according to claim 11, wherein the access port has an airtight portion that maintains an airtight state of a lumen of the access port when the pivot portion is not attached.

17. The multi-degree-of-freedom forceps system according to claim 1, further comprising:
a treatment portion which is attached to the bending portion and is used for tissue treatment,
wherein:
the treatment portion has a pair of forceps pieces that can be opened and closed,
the operating portion has a second operating portion that is connected to the pair of forceps pieces and is configured to open and close the forceps pieces, and
the second operating portion is rotatably attached to the handle body.

18. The multi-degree-of-freedom forceps system according to claim 1, further comprising:
a treatment portion which is attached to the bending portion and is used for tissue treatment,
wherein:
the operating portion has a rotating knob that rotates the treatment portion relative to the insertion portion, and
the rotating knob is connected to the treatment portion at a position closer to a distal end side than a proximal end portion of the insertion portion.

19. The multi-degree-of-freedom forceps system according to claim 1, wherein:
the operating portion has a grip portion that is provided around the joint portion and is elastically deformable, and
the frictional force between the grip portion and the joint portion changes when the grip portion is elastically deformed to change contact pressure with the joint portion.

20. The multi-degree-of-freedom forceps system according to claim 1, wherein the insertion portion is rigid.

* * * * *